(12) United States Patent
Loftsson et al.

(10) Patent No.: US 8,633,172 B2
(45) Date of Patent: Jan. 21, 2014

(54) CYCLODEXTRIN NANOTECHNOLOGY FOR OPHTHALMIC DRUG DELIVERY

(71) Applicants: Thorsteinn Loftsson, Reykjavik (IS); Einar Stefansson, Reykjavik (IS)

(72) Inventors: Thorsteinn Loftsson, Reykjavik (IS); Einar Stefansson, Reykjavik (IS)

(73) Assignee: Oculis EHF, Reykjavik (IS)

( * ) Notice: Subject to any disclaimer, the term of this patent is extended or adjusted under 35 U.S.C. 154(b) by 0 days.

(21) Appl. No.: 13/758,955

(22) Filed: Feb. 4, 2013

(65) Prior Publication Data

US 2013/0142791 A1  Jun. 6, 2013

Related U.S. Application Data

(63) Continuation of application No. 13/014,964, filed on Jan. 27, 2011, now abandoned, which is a continuation of application No. 11/489,466, filed on Jul. 20, 2006, now Pat. No. 7,893,040.

(60) Provisional application No. 60/701,621, filed on Jul. 22, 2005, provisional application No. 60/795,563, filed on Apr. 28, 2006.

(51) Int. Cl.
*A61K 31/724* (2006.01)
*A61K 31/715* (2006.01)

(52) U.S. Cl.
USPC ............... 514/58; 514/54; 514/914; 536/103

(58) Field of Classification Search
USPC .............................. 514/58, 54, 914; 536/103
See application file for complete search history.

(56) References Cited

U.S. PATENT DOCUMENTS

| 5,472,954 A | 12/1995 | Loftsson |
| 2005/0031697 A1 | 2/2005 | Vehige et al. |
| 2005/0234018 A1 | 10/2005 | Lyons et al. |

FOREIGN PATENT DOCUMENTS

| EP | 0 579 435 B1 | 1/1994 |
| EP | 0 709 099 A2 | 5/1996 |
| WO | WO 2004/087100 A2 | 10/2004 |
| WO | WO 2005/105067 A2 | 11/2005 |
| WO | WO 2005/105067 A3 | 11/2005 |

OTHER PUBLICATIONS

Sugrue, "The Pharmacology of Antiglaucoma Drugs", Pharmac. Ther. vol. 43, pp. 91-138, 1989, Maxwell Pergamon Macmillian plc, Great Britain.
Salminen et al., "Disposition of Ophthalmic Timolol in Treated and Untreated Rabbit Eyes. A Multiple and Single Dose Study", Exp. Eye Res., vol. 38, pp. 203-206, 1984, Academic Press Inc. London.
Beeley et al., "Fabrication, implantation, elution, and retrieval of a steroid-loaded polycaprolactone subretinal implant", Journal of biomedical materials research, vol. 73, pp. 437-444, 2005, Wiley Periodicals, Inc., USA.
Myles et al., "Recent progress in ocular drug delivery for posterior segment disease: Emphasis on transscleral iontophoresis", Advanced Drug Delivery Reviews, vol. 57, pp. 2063-2079, 2005, Elsevier B.V. , Netherlands.
Raghava et al., "Periocular routes for retinal drug delivery", Expert Opinion, Drug Delivery, vol. 1, pp. 99-114, 2004, Ashley Publications Ltd., England.
Yasukawa et al., "Intraocular sustained drug delivery using implantable polymeric devices", Advanced Drug Delivery Reviews, vol. 57, pp. 2033-2046, 2005, Elsevier B.V. , Netherlands.
Jonas, "Intravitreal triamcinolone acetonide for treatment of intraocular oedematous and neovascular diseases", Acta Ophthalmologica Scandinavia, vol. 83, pp. 645-663, 2005, Munksgaard, Denmark.
Duan et al., "Cyclodextrin solubilization of the antibacterial agents triclosan and triclocarban: Formation of aggregates and higher-order complexes", International Journal of Pharmaceutics, vol. 297, pp. 213-222, 2005, Elsevier B.V. , Netherlands.
Gonzalez-Gaitano et al., "The Aggregation of Cyclodextrins as Studied by Photon Correlation Spectroscopy", Journal of Inclusion Phenomena and Macrocylclic Chemistry, vol. 44, pp. 101-105, 2002, Kluwer Academic Publishers, The Netherlands.
Loftsson et al., "Cyclodextrins in drug delivery", Expert Opinion, vol. 2, Drug Delivery, pp. 335-351, 2005, Ashley Publications Ltd., London.
Loftsson et al., "Cyclodextrins in ophthalmic drug delivery", Advanced Drug Delivery Reviews, vol. 36, pp. 59-79, 1999, Elsevier B.V. , Netherlands.
Loftsson et al., "The effects of organic salts on the cyclodextrin solubilization of drugs", International Journal of Pharmaceutics, vol. 262, pp. 101-107, 2003, Elsevier B.V. , Netherlands.

(Continued)

*Primary Examiner* — Shaojia Anna Jiang
*Assistant Examiner* — Michael C Henry
(74) *Attorney, Agent, or Firm* — Dentons US LLP

(57) ABSTRACT

The invention provides an ophthalmic composition which is an aqueous suspension comprising drug, cyclodextrin and water, the composition having an aqueous phase of from about 0.1% (w/v) to about 90% (w/v) of the drug in solution, as dissolved free drug and as dissolved drug/cyclodextrin complex(es), and a solid phase of from about 10% (w/v) to about 99.9% (w/v) of the drug as solid drug/cyclodextrin particles, suspended in the aqueous phase; the size of the solid particles being from about 10 nm to about 1 mm, the drug/cyclodextrin particles being capable of dissolving in aqueous tear fluid within 24 hours of application to the eye surface. The aqueous eye suspension can be in the form of eye drops, eye gel or eye mist. Further, the invention provides a method for treating a condition of the posterior segment and/or anterior segment of the eye comprising applying to the eye surface, in an amount which delivers to said segment or segments a therapeutically effective amount of a drug suitable for treating said condition, an ophthalmic composition which is as defined above. Nasal compositions and methods and ophthalmic and nasal compositions in powder form are also provided.

20 Claims, 7 Drawing Sheets

(56) References Cited

OTHER PUBLICATIONS

Loftsson et al., "The effects of water-soluble polymers on cyclodextrins and cyclodextrin solubilization of drugs", J. Drug Del. Sci. Tech, vol. 14, pp. 35-43, 2004, Editions de Santé, France.

Loftsson et al., "Self-Association of Cyclodextrins and Cyclodextrin Complexes", Journal of Pharmaceutical Sciences, vol. 93, No. 5, pp. 1091-1099, Wiley-Liss, Inc and the American Pharmacists Association, USA.

Loftsson et al., "Cyclodextrins in eye drop formulations: enhanced topical delivery of corticosteroids to the eye", Acta Ophthalmologica Scandinavia 2002, vol. 80, pp. 144-150, Munksgaard, Denmark.

Loftsson et al., "Cyclodextrin Solubilization of the Antibacterial Agents Triclosan and Triclocarban: Effect of Ionization and Polymers", Journal of Inclusion Phenomena and Macrocyclic Chemistry, vol. 52, pp. 109-117, 2005, Springer, Netherlands.

Magnusdottir et al., "Self Association and Cyclodextrin Solubilization of NSAIDs", Journal of Inclusion Phenomena and Macrocyclic Chemistry, vol. 44, pp. 213-218, 2002, Kluwer Academic Publishers, The Netherlands.

Mele et al., "Non-covalent associations of cyclomaltooligosaccharides (cyclodextrins) with *trans*-β-carotene in water: evidence for the formation of large aggregates by light scattering and NMR spectroscopy", Carbohydrate Research, vol. 310, pp. 261-267, 1998, Elsevier B.V, Netherlands.

Zimmer et al., "Microspheres and nanoparticles used in ocular delivery systems", Advanced Drug Delivery Reviews, vol. 16, pp. 61-73, 1995, Elsevier B.V, Netherlands.

Kirstinsson et al., "Dexamethasone-Cyclodextrin-Polymer Co-complexes in Aqueous Eye Drops", Investigative Ophthalmology & Visual Science, vol. 37, No. 6, pp. 1199-1203, 1996, Lippincott-Raven Publication, USA.

Loftsson et al., "Evaluation of cyclodextrin solubilization of drugs", International Journal of Pharmaceutics, vol. 302, pp. 18-28, 2005, Elsevier B.V., Netherlands.

Ammar et al., "Cyclodextrins in acetazolamide eye drop formulations", Pharmazie, vol. 53, pp. 559-562, 1998, Govi-Verlag Pharmazeutischer Verlag GmbH Eschborn, Germany.

Loftsson et al., "Topically effective ocular hypotensive acetazolamide and ethoxyzolamide formulations in rabbits", J. Pharm. Pharmacol., vol. 46, pp. 503-504, 1994, Pharmaceutical Press, England.

Loftsson et al., "Cyclodextrin solubilization of benzodiazepines: formulation of midazolam nasal spray", International Journal of Pharmaceutics, vol. 212, pp. 29-40, 2001, published by Elsevier, The Netherlands.

Friðriksdóttir, Hafrú, "Polymer Enhancement of Cyclodextrin Complexation In vivo and In vitro observations," A Doctoral Thesis, 1997, pp. 6-114, University of Iceland, IS.

Rowe, Raymond C., et al., eds., "Cyclodextrins", *Handbook of Pharmaceutical Excipients*, 4th Edition, 2003, pp. 186-190,The Pharmaceutical Press, London, England.

Ysayapant et al., "Effect of 2-Hydroxypropyl-β-cyclodextrin on the Ocular Absorption of Dexamethasone and Dexamethasone Acetate," Pharmaceutical Research, vol. 8, No. 12, pp. 1495-1499.

Written Opinion of the International Searching Authority for corresponding PCT/IB2006/002769.

International Search Report for corresponding PCT/IB2006/002769.

CYCLODEXTRIN NANOTECHNOLOGY FOR OPHTHALMIC DRUG DELIVERY

CROSS-REFERENCE TO RELATED APPLICATIONS

This application is a continuation of U.S. application Ser. No. 13/014,964, filed Jan. 27, 2011, which is a continuation of U.S. application Ser. No. 11/489,466, filed Jul. 20, 2006, now U.S. Pat. No. 7,893,040, which claims the benefit of earlier copending U.S. provisional applications No. 60/701,621, filed Jul. 22, 2005, and No. 60/795,563, filed Apr. 28, 2006, all hereby incorporated by reference in their entireties and relied upon.

FIELD OF THE INVENTION

The invention relates to cyclodextrin nanotechnology for drug delivery, more especially, to cyclodextrin formulations that can effectively deliver therapeutically effective drug amounts to the posterior section of the eye.

BACKGROUND OF THE INVENTION

Cyclodextrins are cyclic oligosaccharides with a hydrophilic outer surface and a somewhat lipophilic central cavity. In aqueous solutions cyclodextrins are able to form inclusion complexes with many drugs by taking up a drug molecule, or more frequently some lipophilic moiety of the molecule, into the central cavity. This property has been utilized for drug formulation and drug delivery purposes. Formation of drug/cyclodextrin inclusion complexes, their effect on the physicochemical properties of drugs and usage in pharmaceutical products has been reviewed (Loftsson, Jarho et al. 2005). For a variety of reasons, including cost, formulation bulk and toxicology, the amount of cyclodextrin that can be included in drug formulations is limited. This is further complicated by the fact that the complexation efficacy of cyclodextrins is, in general, very low and their molecular weight is rather high. Previously it has been shown that complexation efficacy of cyclodextrins can be significantly enhanced by including small amount of a water-soluble polymer in the aqueous complexation medium (Thorsteinn Loftsson, Cyclodextrin complexation, European Patent No.: 0579435 (Mar. 17, 1999); Thorsteinn Loftsson, Cyclodextrin Complexation, U.S. Pat. No. 5,472,954 (Dec. 5, 1995); Thorsteinn Loftsson, Cyclodextrin complexation, European Patent No.: 0579435 (Mar. 17, 1999)). The polymers increase the apparent stability constant of the drug/cyclodextrin complexes through formation of ternary drug/cyclodextrin/polymer complexes. Thus, on the average 40 to 50% less CD is needed when a polymer is present. Furthermore, some studies have shown that drug bioavailability from formulations containing a ternary drug/cyclodextrin/polymer complex is greater than from a comparable drug/cyclodextrin binary complex. In general, the water-soluble polymers improve both pharmaceutical and biological properties of drug/cyclodextrin complexes. Until recently it was generally believed that most drugs form simple 1:1 or 1:2 drug/cyclodextrin inclusion complexes. However recently it has been shown that cyclodextrins and cyclodextrin complexes self-associate to form aggregates and that those aggregates can act as solubilizers themselves (Mele, Mendichi et al. 1998; González-Gaitano, Rodríguez et al. 2002; Magnusdottir, Másson et al. 2002; Loftsson, Másson et al. 2004). There are some indications that the water-soluble polymers and certain organic and inorganic salts enhance the complexation efficiency by stabilizing these aggregates by forming non-inclusion complexes (Loftsson, Matthíasson et al. 2003; Loftsson and Másson 2004; Loftsson, Másson et al. 2004; Duan, Zhao et al. 2005; Loftsson, Össurardóttir et al. 2005). The critical cyclodextrin concentration of the aggregate formation is about 5.4% (w/v) (Duan, Zhao et al. 2005; Loftsson, Össurardóttir et al. 2005). Lysine, polyvinylpyrrolidone and magnesium ions formed non-inclusion complexes resulting in formation of ternary, quaternary and even pentenary complexes in aqueous solutions (Duan, Zhao et al. 2005). The diameter of these self-assembling aggregates has been estimated to be about 6 nm (aggregates of two or three drug/cyclodextrin complexes).

The usage of cyclodextrins in ophthalmic formulation has been reviewed (Loftsson and Järvinen 1999; Loftsson and Stefánsson 2002). Cyclodextrins make it possible to formulate lipophilic drugs in aqueous eye drop solutions. This may be useful for the formulation of a variety of lipophilic drugs that have not been available as eye drops or only in suboptimal formulations. Steroid drugs, including corticosteroids, are a good example of such drugs. They are lipophilic and have only been available in eye drops as prodrugs or suspensions with limited concentration and bioavailability. Likewise, carbonic anhydrase inhibitors have only been available as oral formulation or aqueous eye drop formulation where the pH has to be adjusted to non-physiological values. With cyclodextrins it is possible to increase the concentration of dissolved drug and enhance drug bioavailability and create formulations that offer more effective and less frequent treatment schedules.

Drug Elimination from Pre-Corneal Area.

After ocular instillation, aqueous eye drops will mix with the tear fluid and be dispersed over the eye surface. However, various pre-corneal factors will limit the ocular absorption by shortening corneal contact time of applied drugs. The most important factors are the drainage of installed solution, non-corneal absorption and induced lacrimation. These factors, and the corneal barrier itself, will limit penetration of a topically administered ophthalmic drug. As a result, only few percentages of the applied dose are delivered into the intraocular tissues. The major part (50-100%) of the administered dose will be absorbed into the systemic drug circulation which can cause various side effects. Following instillation of an applied eye-drop (25-50 µl) onto the pre-corneal area of the eye, the greater part of the drug solution is rapidly drained from the eye surface and the solution volume returns to the normal resident tear volume of about 7 µl. Thereafter, the pre-ocular solution volume remains constant, but drug concentration decreases due to dilution by tear turnover and corneal and non-corneal absorption. The value of the first-order rate constant for the drainage of eye drops from pre-corneal area is typically about 1.5 $min^{-1}$ in humans. Normal tear turnover is about 1.2 µl/min in humans (Sugrue 1989). The precorneal half-life of topically applied drugs is between 1 and 3 minutes.

Drug Delivery to the Posterior Segments of the Eye.

Drug delivery to the posterior part of the eye (e.g. to retina, choroid, vitreous and optic nerve) is important for treating several disorders such as age-related macular degeneration, diabetic retinopathy, retinal venous occlusions, retinal arterial occlusion, macular edema, postoperative inflammation, uveitis retinitis, proliferative vitreoretinopathy and glaucoma. Due to anatomic membrane barriers (i.e. cornea, conjunctiva and sclera) and the lachrymal drainage it can be quite challenging to obtain therapeutic drug concentrations in the posterior parts of the eye after topical drug administration. Reaching the posterior part of the eye is even more challenging task because of the anatomical and physiological barriers associated with this part of the eye. Since those barriers cannot be altered with non-invasive methods, the ophthalmic formulations have to be improved in some way to increase the ocular bioavailability. To date, there is no noninvasive, safe and patient-friendly drug delivery system that is specific and effective for the posterior part of the eye. In general, drugs can enter the eye via three distinctive routes, i.e. a) through conjunctiva/sclera after topical application, b) from the anterior part after topical application, and c) from the systemic circulation after topical application, parenteral, oral, and intranasal or other administration route that delivers drug to the blood circulation. Then drugs can be delivered to the eye via invasive methods such as direct drug injection into the vitreous humor or subconjunctival injections. Invasive methods can cause discomfort for the patient and can also lead to complications that are even more serious than the disease being treated. In most cases, topical or systemic administration is used to treat posterior diseases despite limited bioavailability from these formulations.

It is generally accepted that eye drops are ineffective and of little benefit in delivering drugs in therapeutic concentrations to the posterior segment of the eye (Myles et al 2005; Raghava et al 2004; Yasukawa et al 2005). Therefore various approaches have been developed where drugs are injected into the vitreous cavity (Jonas 2005), injected under the conjunctiva or tenon's capsule and various devices invented that may be introduced into the eye (Yasukawa et al 2005). All of these approaches are based on the premise that non-invasive topical methods to effectively deliver drugs, such as corticosteroids, to the posterior segment of the eye are not available, and invasive methods are the only alternative (Myles et al 2005; Raghava et al 2004; Yasukawa et al 2005; Beeley et al 2005).

Microspheres and nanoparticles are colloidal drug carriers in the micro- and submicron range. These systems were developed to overcome solubility problems of poorly soluble drugs as well as for long acting injectable depot formulations and specific drug targeting options. These carriers (without cyclodextrin) were also evaluated for ophthalmic drug delivery purposes over the past 25 years (Zimmer and Kreuter 1995). Nanoparticles formed by surface active cyclodextrin derivatives have been studied but not specifically for topical drug delivery to the eye. Previously, aqueous eye drop suspensions have been studied but in these studies the particles were obtained by including insufficient amounts of cyclodextrin to the formulations, that is the solid particles consisted of relatively pure drug and not drug/cyclodextrin complexes (H. O. Ammar, S. A. El-Nahhas and R. M. Khalil, Cyclodextrins in acetazolamide eye drop formulations, Pharmazie, 53, 559-562 (1998); T. Loftsson, H. Friðriksdóttir, E. Stefánsson, S. Thórisdóttir, Ö. Guðmundsson, and T. Sigthórsson, Topically effective ocular hypotensive acetazolamide and ethoxyzolamide formulations in rabbits, J. Pharm. Pharmacol., 46, 503-504 (1994)). In this present invention the parent α-, β- and γ-cyclodextrin, and their currently acceptable derivatives for pharmaceutical products, are used to form drug containing particles for ophthalmic drug delivery.

REFERENCES

Myles M E, Neumann D M, Hill J M., 2005; Recent progress in ocular drug delivery for posterior segment disease: emphasis on transscleral iontophoresis. *Adv Drug Deliv Rev.* 57(14):2063-79.
Raghava S, Hammond M, Kompella U B (2004), Periocular routes for retinal drug delivery, *Expert Opin Drug Deliv,* 1(1):99-114.
Yasukawa T, Ogura Y, Sakurai E, Tabata Y, Kimura H. (2005), Intraocular sustained drug delivery using implantable polymeric devices, *Adv Drug Deliv Rev.* 13; 57(14):2033-46.
Jonas J B (2005), Intravitreal triamcinolone acetonide for treatment of intraocular oedematous and neovascular diseases, Acta Ophthalmol Scand. 83(6):645-63.
Beeley N R, Rossi J V, Mello-Filho P A, Mahmoud M I, Fujii G Y, de Juan E Jr, Varner S E., (2005) Fabrication, implantation, elution, and retrieval of a steroid-loaded polycaprolactone subretinal implant, *J Biomed Mater Res A.* 15; 73(4):437-44.
Duan, M., N. Zhao, et al. (2005). "Cyclodextrin solubilization of the antibacterial agents triclosan and triclocarban: formation of aggregates and higher-order complexes." Int. J. Pharm. 297: 213-222.
González-Gaitano, G., P. Rodríguez, et al. (2002). "The aggregation of cyclodextrins as studied by photon correlation spectroscopy." *J. Incl. Phenom. Macrocycl. Chem.* 44: 101-105.
Loftsson, T., P. Jarho, et al. (2005). "Cyclodextrins in drug delivery." *Expert Opin. Drug Deliv.* 2: 335-351.
Loftsson, T. and T. Järvinen (1999). "Cyclodextrins in ophthalmic drug delivery."*Adv. Drug Deliv. Rev.* 36: 59-79.
Loftsson, T., K. Matthíasson, et al. (2003). "The effects of organic salts on the cyclodextrin solubilization of drugs." *Int. J. Pharm.* 262: 101-107.
Loftsson, T. and M. Másson (2004). "The effects of water-soluble polymers on cyclodextrins and cyclodextrin solubilization of drugs." *J. Drug Del. Sci. Tech.* 14: 35-43.
Loftsson, T., M. Másson, et al. (2004). "Self-association of cyclodextrins and cyclodextrin complexes." *J. Pharm. Sci.* 93: 1091-1099.
Loftsson, T. and E. Stefánsson (2002). "Cyclodextrins in eye drop formulations: enhanced topical delivery of corticosteroids to the eye." *Acta Ophthalmol. Scand.* 80: 144-150.
Loftsson, T., Í. B. Össurardóttir, et al. (2005). "Cyclodextrin solubilization of the antibacterial agents triclosan and triclocarban: effect of ionization and polymers." *J. Incl. Phenom. Macroc. Chem.* 52: 109-117.
Magnusdottir, A., M. Másson, et al. (2002). "Self association and cyclodextrin solubilization of NSAIDs." *J. Ind Phenom. Macroc. Chem.* 44: 213-218.
Mele, A., R. Mendichi, et al. (1998). "Non-covalent associations of cyclomaltooligosaccharides (cyclodextrins) with trans-β-carotene in water: evidence for the formation of large aggregates by light scattering and NMR spectroscopy." *Carboh. Res.* 310: 261-267.
Sugrue, M. F. (1989). "The pharmacology of antiglaucoma drugs." *Pharm. Ther.* 43: 91-138.
Zimmer, A. and J. Kreuter (1995). "Microspheres and nanoparticles used in ocular delivery systems."*Adv. Drug Deliv. Rev.* 16: 61-73.

SUMMARY

The present inventors have found that the generally acceptable dogma detailed above in the section entitled Drug delivery to the posterior segments of the eye, that is, that eye drops are ineffective in delivering drugs to the posterior segments, in particular to the retina, vitreous and optic nerve, is not correct. On the contrary, the present inventors have invented a drug delivery platform that can effectively deliver drugs, such as dexamethasone, to the posterior segments of the eye in therapeutically effective concentrations by topical administration to the eye. Retinal diseases may accordingly effectively be treated by drugs delivered topically to the eye as eye drop suspensions or as solid water-soluble particles.

The invention thus provides an ophthalmic composition which is an aqueous suspension comprising drug, cyclodextrin and water, the composition having an aqueous phase of from about 0.1% (w/v) to about 90% (w/v) of the drug in solution, as dissolved free drug and as dissolved drug/cyclodextrin complex(es) and a solid phase of from about 10% (w/v) to about 99.9% (w/v) of the drug as solid drug/cyclodextrin particles, suspended in the aqueous phase; the size of the solid particles being from about 10 nm to about 1 mm, the drug/cyclodextrin particles being capable of dissolving in aqueous tear fluid, the cyclodextrin comprising at least one natural cyclodextrin selected from the group consisting of α-cyclodextrin, β-cyclodextrin and γ-cyclodextrin. The aqueous eye suspension can be in the form of eye drops, eye gel or eye mist.

In another aspect, the invention provides a new use for cyclodextrin in the preparation of an aqueous eye suspension as defined in the preceding paragraph, for drug delivery to the posterior segments of the eye in a therapeutically effective amount for treating a condition of said segment.

Further, the invention provides a method for treating a condition of a posterior segment of the eye comprising applying to the eye surface, in an amount which delivers to said posterior segment a therapeutically effective amount of a drug suitable for treating said condition, an ophthalmic composition which is an aqueous suspension, preferably an aqueous drop formulation, but alternatively an aqueous gel or mist/spray formulation, comprising drug, cyclodextrin and water, the formulation having an aqueous phase of from about 0.1% (w/v) to about 90% (w/v) of the drug in solution, as dissolved free drug and as dissolved drug/cyclodextrin complex(es), and a solid phase of from about 10% (w/v) to about 99.9% (w/v) of the drug as solid drug/cyclodextrin particles suspended in the aqueous phase; the size of the solid particles being from about 10 nm to about 1 mm, the drug/cyclodextrin particles being capable of dissolving in aqueous tear fluid, the cyclodextrin comprising at least one natural cyclodextrin selected from the group consisting of α-cyclodextrin, β-cyclodextrin and γ-cyclodextrin.

The invention also provides a nasal composition which is an aqueous suspension comprising drug, cyclodextrin and water, the composition having an aqueous phase of from about 1% (w/v) to about 95% (w/v) of the drug in solution, as dissolved free drug and as dissolved drug/cyclodextrin complex(es), and a solid phase of from about 5% (w/v) to about 99% (w/v) of the drug as solid drug/cyclodextrin particles, the particle size of the particles in the solid phase being from about 10 nm to about 1 mm, the drug/cyclodextrin particles being capable of dissolving in nasal mucous fluid within about 24 hours after application to the nasal mucosa, the cyclodextrin comprising at least one natural cyclodextrin selected from the group consisting of α-cyclodextrin, β-cyclodextrin and γ-cyclodextrin. The nasal composition can be in the form of drops, spray/mist or gel.

In yet another aspect, the invention provides a new use for cyclodextrin in the preparation of an aqueous nasal suspension as defined in the preceding paragraph, for drug delivery to the nose in a therapeutically effective amount for drugs suited to nasal administration.

The invention also provides a method for treating a condition susceptible to treatment by nasal drug administration comprising applying to the nasal mucosa a nasal composition as defined above.

Still further, the present invention provides a method for not only treating a condition of the posterior segment of the eye but also a method for treating the anterior segment of the eye, and a method for treating a condition of both the posterior and anterior segments of the eye, comprising applying to the eye surface, in an amount which delivers to said segment or segments a therapeutically effective amount of a drug suitable for treating said condition, an ophthalmic composition which is an aqueous suspension as defined above.

The invention also provides the ophthalmic composition as a powder which is a lyophilized or spray-dried form of the ophthalmic suspension form as defined above. The powder form of the ophthalmic composition is useful in treating the same ophthalmic conditions treated with the aqueous suspension form of the ophthalmic composition.

The invention further provides the nasal composition as a powder which is a lyophilized or spray-dried form of the aqueous suspension form of the nasal aqueous suspension as defined above. The powder form of the nasal composition is useful in treating the same conditions treated with the aqueous suspension form of the nasal composition.

DETAILED DESCRIPTION

Figure 1:
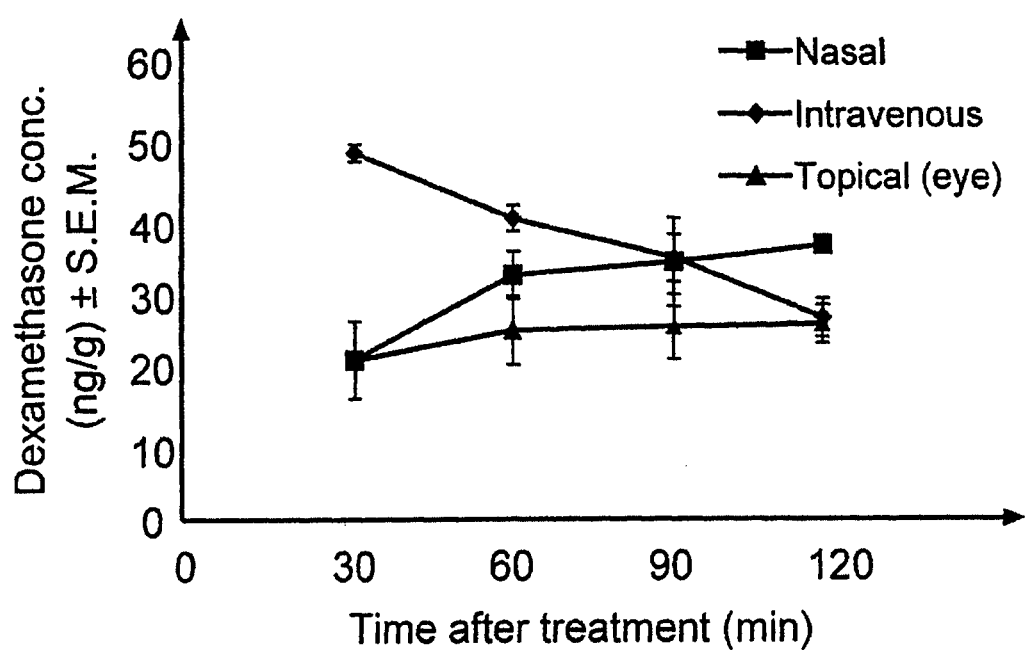
FIG. 1 is a plot of dexamethasone blood levels, in ng/g, against time post treatment, in minutes, following intranasal, intravenous and ophthalmic administration to rabbits of a 0.5% dexamethasone eye drop solution prepared as described in Experiment 1 below (prior art randomly methylated β-cyclodextrin/dexamethasone solution).

The following definitions and explanations are applicable to this application.

An ocular condition is a disease, ailment or other condition which affects or involves the eye or one of the parts or regions of the eye. Broadly speaking, the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves one or more of the following: the conjunctiva, the cornea, the anterior chamber, the iris, the posterior chamber (behind the retina but in front of the posterior wall of the lens capsule), the lens, or the lens capsule, and blood vessels and nerves which vascularize or innervate an anterior ocular region or site. A posterior ocular condition is a disease, ailment or condition which primarily affects or involves a posterior ocular region or site such as the choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition such as, for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

An anterior ocular condition can include a disease, ailment or condition such as, for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

The present invention is concerned with and directed to ophthalmic compositions for topical drug delivery to the eye (s) and to methods for the treatment of an ocular condition, such as an anterior ocular condition or a posterior ocular condition or an ocular condition which can be characterized as both an anterior ocular condition and a posterior ocular condition.

Macular degeneration, such as age-related macular degeneration ("AMD") is a leading cause of blindness in the world. It is estimated that thirteen million Americans have evidence of macular degeneration. Macular degeneration results in a breakdown of the macula, the light-sensitive part of the retina responsible for the sharp, direct vision needed to read or drive. Central vision is especially affected. Macular degeneration is diagnosed as either dry (atrophic) or wet (exudative). The dry form of macular degeneration is more common than the wet form of macular degeneration, with about 90% of AMD patients being diagnosed with dry AMD. The wet form of the disease usually leads to more serious vision loss. Macular degeneration can produce a slow or sudden painless loss of vision. The cause of macular degeneration is not clear. The dry form of AMD may result from the aging and thinning of macular tissues, depositing of pigment in the macula, or a combination of the two processes. With wet AMD, new blood vessels grow beneath the retina and leak blood and fluid. This leakage causes retinal cells to die and creates blind spots in central vision.

Macular edema ("ME") can result in a swelling of the macula. The edema is caused by fluid leaking from retinal blood vessels. Blood leaks out of the weak vessel walls into a very small area of the macula which is rich in cones, the nerve endings that detect color and from which daytime vision depends. Blurring then occurs in the middle or just to the side of the central visual field. Visual loss can progress over a period of months. Retinal blood vessel obstruction, eye inflammation, and age-related macular degeneration have all been associated with macular edema. The macula may also be affected by swelling following cataract extraction. Symptoms of ME include blurred central vision, distorted vision, vision tinted pink and light sensitivity. Causes of ME can include retinal vein occlusion, macular degeneration, diabetic macular leakage, eye inflammation, idiopathic central serous chorioretinopathy, anterior or posterior uveitis, pars planitis, retinitis pigmentosa, radiation retinopathy, posterior vitreous detachment, epiretinal membrane formation, idiopathic juxtafoveal retinal telangiectasia, Nd:YAG capsulotomy or iridotomy. Some patients with ME may have a history of use of topical epinephrine or prostaglandin analogs for glaucoma. The first line of treatment for ME is typically anti-inflammatory drops topically applied.

Macular edema is a non-specific response of the retina to a variety of insults. It is associated with a number of diseases, including uveitis, retinal vascular abnormalities (diabetic retinopathy and retinal vein occlusive disease), a sequelae of cataract surgery (post-cataract cystoid macular edema), macular epiretinal membranes, and inherited or acquired retinal degeneration. Macular edema involves the breakdown of the inner blood retinal barrier at the level of the capillary endothelium, resulting in abnormal retinal vascular permeability and leakage into the adjacent retinal tissues. The macula becomes thickened due to fluid accumulation resulting in significant disturbances in visual acuity.

Macular edema may occur in patients having diseases causing cumulative injury over many years, such as diabetic retinopathy, or as a result of more acute events, such as central retinal vein occlusion or branch retinal vein occlusion.

In some cases, macular edema resolves spontaneously or with short-term treatment. Therapeutic choices for macular oedema depend on the cause and severity of the condition. Currently there are no approved pharmacological therapies for macular edema.

Techniques such as intravitreal injection of a drug have shown promising results, but due to the short intraocular half-life of the active agents, such as glucocorticoids (approximately 3 hours), intravitreal injections must be frequently repeated to maintain a therapeutic drug level. In turn, this repetitive process increases the potential for side effects such as retinal detachment, endophthalmitis, and cataracts.

Potent corticosteroids such as dexamethasone suppress inflammation by inhibiting edema, fibrin deposition, capillary leakage and phagocytic migration, all key features of the inflammatory response. Corticosteroids prevent the release of prostaglandins, some of which have been identified as mediators of cystoid macular edema. Additionally, corticosteroids including dexamethasone have been shown to inhibit the expression of vascular endothelial growth factor (VEGF), a cytokine which is a potent promoter of vascular permeability.

The use of dexamethasone to date, by conventional routes of administration, has yielded limited success in treating retinal disorders, including macular edema, largely due to the inability to deliver and maintain adequate quantities of the drug to the posterior segment without resultant toxicity. After usual topical administration of dexamethasone, only about 1% reaches the anterior segment, and only a fraction of that amount moves into the posterior segment. Although intravitreal injections of dexamethasone have been used, the exposure to the drug is very brief as the half-life of the drug within the eye is approximately 3 hours. Periocular and posterior sub-Tenon's injections of dexamethasone also have a short term treatment effect.

"Glaucoma" means primary, secondary and/or congenital glaucoma. Primary glaucoma can include open angle and closed angle glaucoma. Secondary glaucoma can occur as a complication of a variety of other conditions, such as injury, inflammation, vascular disease and diabetes.

"Inflammation-mediated" in relation to an ocular condition means any condition of the eye which can benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion.

"Injury" or "damage" are interchangeable and refer to the cellular and morphological manifestations and symptoms resulting from an inflammatory-mediated condition, such as, for example, inflammation.

"Posterior ocular condition" means a disease, ailment or condition which affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Steroidal anti-inflammatory agent" and "anti-inflammatory steroid" and "glucocorticoid" are used interchangeably herein, and are meant to include steroidal agents, compounds or drugs which reduce inflammation when administered at a therapeutically effective level.

"Therapeutic levels" or "therapeutic amount" or "effective amount" means an amount or a concentration of an active agent that has been locally delivered to an ocular region that is appropriate to safely treat an ocular condition so as to reduce or inhibit or prevent a symptom of an ocular condition.

The active agent for use in the ophthalmic compositions of the invention can be selected from the group consisting of ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, steroids (such as steroidal anti-inflammatory agents), antihypertensives, pressors, antibacterials, antivirals, antifungals, antiprotozoals, anti-infective agents, antitumor agents, antimetabolites, and antiangiogenic agents. Thus, the active agent can be, for example, cortisone, dexamethasone, fluocinolone, hydrocortisone, methylprednisolone, prednisolone, prednisone, triamcinolone, or any anti-inflammatory derivative thereof.

The ophthalmic compositions of the invention typically vary according to the preferred drug release profile, the particular active agent used, the condition being treated, and the medical history of the patient. Active agents that may be used include, but are not limited to, ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, and antiangiogenic agents.

In one variation the active agent is methotrexate. In another variation, the active agent is retinoic acid. In a preferred variation, the anti-inflammatory agent is a nonsteroidal anti-inflammatory agent. Nonsteroidal anti-inflammatory agents that may be used include, but are not limited to, aspirin, diclofenac, flurbiprofen, ibuprofen, ketorolac, naproxen, and suprofen. In a more preferred variation, the anti-inflammatory agent is a steroidal anti-inflammatory agent.

Steroidal Anti-Inflammatory Agents

The steroidal anti-inflammatory agents that may be used in the ocular compositions and methods of the invention include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, etiprednol dicloacetate, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives having anti-inflammatory activity.

In one variation, cortisone, dexamethasone, fluocinolone, hydrocortisone, methylprednisolone, prednisolone, prednisone, and triamcinolone, and their derivatives, are preferred steroidal anti-inflammatory agents. In another preferred variation, the steroidal anti-inflammatory agent is dexamethasone. In another variation, the composition includes a combination of two or more steroidal anti-inflammatory agents.

Other agents may be employed in the formulation for a variety of purposes. For example, buffering agents and preservatives may be employed. Preservatives which may be used include, but are not limited to, sodium bisulfate, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

Examples of medical conditions of the eye which may be treated by the compositions and methods of the invention include, but are not limited to, uveitis, macular edema, macular degeneration, retinal detachment, ocular tumors, fungal or viral infections, multifocal choroiditis, diabetic retinopathy, proliferative vitreoretinopathy (PVR), sympathetic opthalmia, Vogt Koyanagi-Harada (VKH) syndrome, histoplasmosis, uveal diffusion, and vascular occlusion. In one variation, the compositions are particularly useful in treating such medical conditions as uveitis, macular edema, vascular occlusive conditions, proliferative vitreoretinopathy (PVR), and various other retinopathies. See also the discussion of drugs and conditions hereinabove.

Microparticles for Ophthalmic and Nasal Drug Delivery

This invention relates to enhanced topical drug delivery into eye obtained by maintaining the tear fluid saturated with the drug for enhanced duration of time.

The driving force for one-dimensional diffusion is the gradient of chemical potential along the direction of diffusion, that is, spontaneous flow from a region of higher chemical potential to one of lower chemical potential. Maximum chemical potential of a given drug is obtained when it forms a saturated solution, for example when the drug forms a saturated solution in the tear fluid. When the tear fluid is saturated with the drug then the drug molecules have maximum tendency to partition from the fluid into cornea, slera and other tissues that are in contact with the tear fluid. These tissues form hydrophilic or lipophilic membranes. Drug diffusion through these membranes is also driven by the gradient of chemical potential within the membrane and, thus, high drug concentration at the membrane surface will enhance drug delivery through the membrane. Under normal conditions drugs that are administered to the eye as aqueous eye drop solutions will rapidly be diluted and washed from the eye surface by the constant flow of tear fluid. Drug dilution on the eye surface reduces drug flow from the surface into the eye. Many ophthalmic drugs are lipophilic compounds with limited aqueous solubility. Such drugs are sometimes administered as aqueous eye drop suspensions and this will result in somewhat sustained drug concentrations at the eye surface. However, due to their low water-solubility their absorption from the eye surface into the eye will be dissolution rate limited, that is drug absorption into the eye will be hampered by the slow dissolution of the solid drug. Administration of such lipophilic drugs as more water-soluble drug/cyclodextrin complexes will increase the dissolution rate of the solid drug in the tear fluid preventing dissolution rate limited drug absorption. Particles in an ophthalmic eye drop suspension are washed more slowly than dissolved drug molecules from the eye surface, partly due to inherent mucoadhesion of the particles. The particles attach themselves to the mucus fraction of the tear film. Furthermore, the amount of dissolved drug in the tear fluid can be controlled by combining natural cyclodextrins and more water-soluble cyclodextrin derivatives in the aqueous eye drop formulation. The hydrophilic cyclodextrins (such as the natural $\alpha$-, $\beta$- and $\gamma$-cyclodextrin and their hydroxypropyl and sulfobutyl ether derivatives) enhance drug delivery from aqueous vehicles through lipophilic biological membranes by constantly delivering dissolved drug molecules to the membrane surface. These cyclodextrins have negligible effect on the chemical composition and structure of the lipophilic membranes. Enhanced absorption is obtained through introduction of more favorable physicochemical conditions for passive drug diffusion. Administration of the aqueous drug/cyclodextrin eye drop suspensions, as well as solid drug/cyclodextrin complexes, will ensure constant high concentrations of dissolved drug in the aqueous tear fluid (sustained saturated drug solution in the tear fluid).

Mathematical Explanation for Absorption of Drugs from the Aqueous Eye Surface Through the Sclera or Cornea into the Eye (or from the Aqueous Nasal Mucosa into the Systemic Circulation):

Although many biological membranes contain specialized transport systems that assist passage of some selected compounds, most drugs permeate these membranes, transcellular or paracellular, via passive diffusion. The fundamental equation describing passive drug transport through the membranes is based on Fick's first law:

$$J = P \cdot C_{Aq} \quad (1)$$

where J is the drug flux through a membrane (mass/area/time), P is the permeability coefficient of the drug through the lipophilic membrane and $C_{Aq}$ is the drug concentration at the aqueous exterior. The permeability coefficient is defined as:

$$P = \frac{D \cdot K}{h} \quad (2)$$

where D is the diffusion coefficient of the drug within the membrane, K is the partition coefficient of the drug from the aqueous tear fluid into membrane and h is the effective thickness of the membrane. The equations show that for a drug molecule to be successfully delivered through a membrane, the drug must possess sufficient aqueous solubility (or high $C_{Aq}$ value) but at the same time the drug must possess sufficient lipophilicity to be able to partition from the aqueous exterior into the lipophilic membrane (or high K value). Finally, the diffusion coefficient can be estimated from the Stokes-Einstein equation:

$$D = \frac{R \cdot T}{6\pi \cdot \eta \cdot r \cdot N} \quad (3)$$

where R is the molar gas constant, T is the absolute temperature, $\eta$ is the apparent viscosity within the unstirred water layer or the lipophilic membrane, r is the radius of the permeating drug molecule, and N is Avogadro's number.

The dissolution rate (dM/dt) of solid particles is described by the Noyes-Whitney equation:

$$\frac{dM}{dt} = \frac{D \cdot S}{h_D}(C_s - C) \quad (4)$$

where M is the mass of dissolved drug, D is the diffusion coefficient of the drug in the aqueous tear fluid, S is the total surface area of the solid drug particles, $h_D$ is the thickness of the diffusion layer at the particle surface, $C_S$ is the saturation solubility of the drug in the aqueous fluid, and C is the drug concentration in the bulk solution at time t. The dissolution rate is proportional to both S and $C_S$, and $C_S$ is influenced by composition of the aqueous dissolution medium.

As noted in the BACKGROUND OF THE INVENTION hereinabove, various pre-corneal factors will limit the ocular absorption by shortening corneal contact time of applied drugs. The most important factors are the drainage of installed solution, non-corneal absorption and induced lacrimation. These factors, and the corneal barrier itself, will limit penetration of a topically administered ophthalmic drug. As a result, only few percentages of the applied dose are delivered into the intraocular tissues. The major part (50-100%) of the administered dose will be absorbed into the systemic blood circulation which can cause various side effects. Following instillation of an applied eye-drop (25-50 μl) onto the pre-corneal area of the eye, the greater part of the drug solution is rapidly drained from the eye surface and the solution volume returns to the normal resident tear volume of about 7 μl. Thereafter, the pre-ocular solution volume remains constant, but drug concentration decreases due to dilution by tear turn-over and corneal and non-corneal absorption. The value of the first-order rate constant for the drainage of eye drops from pre-corneal area is typically about 1.5 min$^{-1}$ in humans. Normal tear turnover is about 1.2 μl/min in humans (Sugrue 1989). The precorneal half-life of topically applied drugs is between 1 and 3 minutes. The present invention addresses these problems as follows:

Due to their size, the water-soluble drug/cyclodextrin microparticles will not be washed away from the eye surface but adhere to the surface and the surrounding tissue. The particles will dissolve rapidly enough to maintain the aqueous tear fluid saturated with the drug, i.e. the $C_{Aq}$ in Eq. 1 will not decrease during drainage of the eye. Particles of lipophilic drugs, with limited solubility in water (i.e. low $C_s$ in Eq. 4), will dissolve very slowly in the aqueous tear fluid. Conventional suspensions, even in micronized form, will not possess sufficient rapid dissolution rates (i.e. dM/dt in Eq. 4) to maintain drug saturation of the aqueous tear fluid. Formulating the drug as more water-soluble drug/cyclodextrin complexes (i.e. high $C_s$ in Eq. 4) in a microparticle (i.e. with a large S in Eq. 4) will ensure rapid drug dissolution. This will maintain drug saturation of the aqueous tear fluid (i.e. high $C_{Aq}$ in Eq. 1). Cyclodextrin complexation will not change the lipophilicity (i.e. K in Eq. 2) of the drug and thus the cyclodextrin complexation will not affect the intrinsic ability of the drug molecules to permeate the lipophilic membrane (i.e. cyclodextrin complexation will not change P in Eq. 1). Consequently this novel formulation technology will not only enhance the flux (J) of drug into the eye but also reduce the amount of drug reaching the systemic circulation via, for example, nasal absorption. This novel ophthalmic (or nasal) formulation will enhance topical drug delivery into the eye, i.e. enhance ophthalmic (or nasal) drug availability and at the same time reduce the relative amount of drug reaching the systemic circulation (i.e. reduce systemic drug availability). The result is targeted drug delivery to the eye (or to the nasal mucosa).

To limit or control the drug dissolution rate (i.e. dM/dt in Eq. 4), natural cyclodextrins are used. The microparticles will then consist of drug/α-cyclodextrin, drug/β-cyclodextrin or drug/γ-cyclodextrin complexes. Such complexes are more water-soluble than the lipophilic drugs but less soluble than corresponding drug complexes of the cyclodextrin derivatives, such as drug complexes of 2-hydroxypropyl-β-cyclodextrin, 2-hydroxypropyl-γ-cyclodextrin, randomly methylated β-cyclodextrin and sulfobutylether β-cyclodextrin. These very water-soluble cyclodextrin derivatives are used to form aqueous eye drop solutions of lipophilic drugs. However, in some cases small amounts of these very water-soluble cyclodextrin derivatives are included in the aqueous media containing the solid drug/cyclodextrin particles in order to increase further the concentration of dissolved drug (i.e. high $C_{Aq}$ in Eq. 1) in the aqueous tear fluid. Alternatively, small amounts of these very water-soluble cyclodextrin derivatives are present in the solid particles to enhance further the drug dissolution (i.e. to increase $C_S$ and consequently dM/dt in Eq. 4).

According to Eq. 3, the diffusion coefficient (D) of a permeating molecule is related to their size (i.e. their radius (r) in Eq. 3). The cyclodextrin molecules are large (i.e. have a large r) and hydrophilic (i.e. have a small K in Eq. 2) and, thus, do not easily permeate biological membranes such as corneal and sclera. Thus, the dissolved cyclodextrin molecules will not permeate into the eye, only the smaller lipophilic drug molecules.

We thus use micro- and nano-systems (micro- or nano-aggregates or solid micro- or nanoparticles), consisting of cyclodextrins, drugs and various excipients, which due to their size and/or surface charge, possess mucoadhesive properties that results in enhanced drug absorption into the eye. Typical eye drop formulation will consist of an aqueous drug suspension containing solid drug/cyclodextrin complexes, water-soluble polymers (such as hydroxypropyl methylcellulose, and other cellulose derivatives, and polyvinylpyrrolidone), metal ions (such as magnesium ions) and/or organic salts (such as sodium acetate and sodium citrate), where such additives are used to stabilize the system and lend it enhanced mucoadhesive properties. These are binary, ternary and quaternary drug/cyclodextrin inclusion and/or non-inclusion complexes. It is also possible to dry (e.g. lyophilize) the eye drop suspension and administer solid complex powder to the eye. The composition of the complexes can be as follows:

Drug as used herein refers to a pharmacologically active/useful ingredient whose solubility in water is less than 20 mg/ml, typically less than 1 mg/ml at physiologic pH. Suitable drugs include those noted hereinabove, particularly corticosteroids such as dexamethasone, hydrocortisone, acecortane acetate, prednisolone, triamcinolone, fluorometholone, medrysone, rimexolone, loteprednol etabonate, etiprednol dicloacetate and triamcinolone acetonide; other steroids such as pregnanolone, testosterone and estradiol; carbonic anhydrase inhibitors like acetazolamide, dorzolamide, methazolamide, ethoxyzolamide and brinzolamide; antimicrobial agents such as trimethoprim and ciprofloxacin; GABAergic drugs, for example benzodiazepines such as alprazolam, diazepam, brotizolam, chlordiazepoxide, clobazam, clonazepam, clorazepam, demoxazepam, flumazenil, furazepam, halazepam, midazolam, nordazepam, medazepam, nitrazepam, oxazepam, medazepam, lorazepam, prazepam, quazepam, timezepam, lorazolam and triazolam; and other GABAergic drugs such as baclofen, tiagabine, valproic acid, progabide, muscimol, etomidate, propofol and vigabatrin; nonsteroidal anti-inflammatory agents such as naproxen and many others, including ketoprofen, and various other drugs such as cyclosporine A and prostaglandins such as latanoprost, as well as other drugs for treatment of diseases listed in Table 1.

TABLE 1

Disorders affecting the posterior segment of the eye.

| Classification | Examples | Target tissue and drugs |
|---|---|---|
| Degenerative diseases | Age-related macular degeneration, juvenile macular degeneration, retinitis pigmentosa and other tapitoretinal degenerations | Retina, retinal pigment epithelium and choroid Corticosteroids: for example, triamcinolone, dexamethasone, anecortave acetate (Alcon) Growth factors Growth factor inhibitors (anti-growth factors): for example, Macugen ® (Pfizer), Avastin ®, Lucentis ® (Genentech) |

TABLE 1-continued

Disorders affecting the posterior segment of the eye.

| Classification | Examples | Target tissue and drugs |
|---|---|---|
| Vascular diseases | Diabetic retinopathy, retinal vein or arterial occlusion, retinopathy of prematurity, age-related macular degeneration, sickle cell retinopathy | Retina, retinal blood vessels, iris, choroid<br>Carbonic anhydrase inhibitors: for example, dorzolamide, acetazolamide, ethoxyzolamide, metazolamide<br>GABA agonists (GABAergic agents): for example, benzodiazepines such as diazepam, vigabatrin and other GABAergics |
| Inflammatory diseases | Uveitis, retinitis, postoperative inflammation, phacogenic inflammation | Uveal tissues, sclera, iris, retina, vitreous humor, lens and lens fragments, anterior chamber<br>Corticosteroids: for example, triamcinolone, dexamethosone<br>Antibiotics<br>Cyclosporin<br>Anti-inflammatories |
| Proliferative diseases | Proliferative vitreoretinopathy, retinopathy of prematurity | Vitreous, retina<br>Corticosteroids: for example, triamcinolone, dexamethosone, anecortave acetate (Alcon)<br>Growth factor inhibitors (anti-growth factors): for example, AG013958 (Pfizer) and Macugen ® (Pfizer), Avastin ®, Lucentis ® (Genentech)<br>Antiproliferative (cancer) drugs: for example, daunorubicin, mitomycin C, 5-fluorouracil (5-FU) |
| Infectious diseases | Endophthalmitis, retinitis, uveitis | Vitreous, retina, uvea<br>Antibiotics<br>Anti-inflammatories<br>Corticosteroids: for example, triamcinolone, dexamethasone |
| Others | Glaucoma, optic neuritis | Optic nerve, retina<br>Carbonic anhydrase inhibitors: for example, dorzolamide, acetazolamide, ethoxyzolamide, metazolamide<br>GABA agonists: for example, benzodiazepines such as diazepam, vigabatrin and other GABAergics<br>Other glaucoma drugs: for example, beta blockers such as timolol and betaxolol |

Thus, additional suitable drugs include growth factor inhibitors, such as pegaptanib (Macugen®), a vascular endothelial growth factor antagonist oligonucleotide, bevocizumab (Avastin®), an angiogenesis inhibitor, ranibizumab (Lucentis®), a humanized anti-vascular endothelial growth factor (VEGF) antibody fragment and AG013958, a growth factor inhibitor undergoing clinical trials for wet ADM; and antiproliferative cancer drugs, for example, daunorubicin, mitomycin C and 5-fluorouracil, which can prevent or inhibit scar tissue formation, for example, after glaucoma surgery; as well as drugs for the treatment of glaucoma, such as beta-blockers, for example timolol and betaxolol. Yet other suitable drugs include antibiotics and antiviral agents. Particularly for nasal administration, additional useful drugs include anti-migraine drugs, for example, pizotifen, clonidine or sumatriptan; and narcotic analgesics, for example fentanyl or morphine.

The amount of drug used will be an amount effective to treat the condition for which the drug is administered, for example, in the case of an anti-inflammatory steroid or NSAID (non-steroidal anti-inflammatory drug), an anti-inflammatory effective amount; in the case of a carbonic anhydrase inhibitor, a carbonic anhydrase inhibitory effective amount; in the case of an anti-glaucoma agent, an anti-glaucoma effective amount; in the case of a drug administered to inhibit scar tissue, an effective scar tissue-inhibiting amount; in the case of a growth factor inhibitor, an effective growth antagonizing amount, and so forth. Various conditions to be treated are discussed in detail hereinabove.

Cyclodextrin as employed herein is usually from about 0.25 to about 40% (w/v), typically from about 2 to about 20 or about 25% (w/v). Suitable cyclodextrins are the natural cyclodextrins, $\alpha$-, $\beta$- and $\gamma$-cyclodextrin; included as well may be their pharmaceutically acceptable derivatives such as the hydroxyalkyl derivatives of $\alpha$-, $\beta$- and $\gamma$-cyclodextrin (especially the hydroxyethyl and hydroxypropyl derivatives of $\beta$-cyclodextrin and $\gamma$-cyclodextrin), randomly methylated $\beta$-cyclodextrin, sulfobutyl ether $\beta$-cyclodextrin, sulfobutyl ether $\gamma$-cyclodextrin, and the so-called branched $\beta$- and $\gamma$-cyclodextrin derivatives such as glucosyl-$\beta$-cyclodextrin and glucosyl-$\gamma$-cyclodextrin. The natural cyclodextrins are either used alone or in a mixture of two or more; by way of non-limiting example, a mixture of the natural $\gamma$-cyclodextrin and the more water-soluble hydroxypropyl $\gamma$-cyclodextrin, or $\gamma$-cyclodextrin and sulfobutyl ether $\gamma$-cyclodextrin, or $\beta$-cyclodextrin and hydroxypropyl-$\beta$-cyclodextrin or $\beta$-cyclodextrin and sulfobutyl ether $\beta$-cyclodextrin. The relative amount of dissolved drug in the aqueous eye suspensions can be adjusted by using mixtures of cyclodextrins which have somewhat limited solubility in water and more water-soluble cyclodextrins. Thus, the cyclodextrins are both used as solubilizers and to obtain sustained drug delivery after topical administration.

Water-soluble polymer as used herein is usually from 0 to about 5% (w/v), typically from about 0.1 to about 1% (w/v). Suitable polymers are, for example, methylcellulose, hydroxyethyl cellulose, hydroxypropyl cellulose, hydroxypropyl methylcellulose, hydroxypropyl ethylcellulose, sodium carboxymethylcellulose, polyvinyl alcohol, polyvinylpyrrolidone, polyethylene glycol, poly(methyl methacrylate), polycarbophil, gelatin, alginate, poly(acrylic acid), polyethylene oxide and chitosan or a derivative of one of the foregoing. The purpose of the polymers are, for example, to stabilize the nano- and microparticles in the aqueous environment, to enhanced the drug complexation efficiency, to increase the viscosity of the aqueous formulation, to obtain or enhance mucoadhesion, and to enhance sustainability of the drug delivery into the eye. The gel formulations of the invention will contain larger amounts of polymers of this type.

Metal ions, or metal salts as used herein are usually from 0 to about 5% (w/v), typically from 0 to about 2% (w/v). Suitable metal ions are divalent magnesium cations (for example, in the form of $MgCl_2.6H_2O$) and other di- and trivalent cations such as calcium, copper and iron. The metal ions form complexes with various drugs as well as with cyclodextrins. The metal ions/salts are used, for example, to solubilize cyclodextrins, drugs and drug/cyclodextrin complexes, to render surface charge to the nano- and microparticles, and to stabilize the particles.

Organic salts as used herein are usually from 0 to about 5% (w/v), typically from 0 to about 3% (w/v). Suitable organic salts are, for example, sodium or potassium salts of acetic acid, glutaric acid, tartaric acid, lactic acid, ascorbic acid and citric acid, as well as amino acids such as lysine. The salts are, for example, used to enhance the cyclodextrin solubilization of drugs, to stabilize the particles and to render surface charge to the nano- and micro-particles.

With respect to the amount of water in the instant formulations, the following general guidance can be given:

1. Free-Flowing Aqueous Eye Drop Suspensions:

These generally comprise from about 0.5 to about 20% (w/v) of solid particles dispersed in a vehicle containing from about 80 to about 99.5% (w/v) water. Viscosity is below 50 centiPoise, typically between 2 to 15 centiPoise.

2. Semi-Solid Aqueous Suspensions (e.g. Paste and Gel):

In general, such formulations comprise from about 20 to about 50% (w/v) of solid particles dispersed in a vehicle containing from about 50 to about 80% (w/v) water.

3. Solid Particles

Solid particle powder in general contains less than about 20% (w/v) water, typically less than about 7% (w/v) water. Cyclodextrins and cyclodextrin complexes are hygroscopic and thus the solid particles will easily absorb small amount of water from the environment. When stored in the lab in an open container, cyclodextrins contain from between about 5 and to about 10% (w/v) water.

Insofar as concerns particle size, previous cyclodextrin eye drop formulations were clear transparent aqueous solutions. The present invention provides non-transparent suspensions or suspensions that are clearly not fully transparent. In general, it is recommended that particles in ophthalmic suspensions should be less than 10 μm in diameter to minimize irritation to the eye (Remington. *The Science and Practice of Pharmacy*, 21$^{st}$ Ed., Lippincott Williams & Winkins, Philadelphia 2006, p. 856). However, in the present invention the particle size is up to 100 μm but the particles cause insignificant irritation since they dissolve relatively rapidly in the aqueous tear fluid. Further information relating to particle size is shown in Experiment 5 hereinbelow.

The compositions may further comprise at least one buffer salt and/or at least one preservative. The eye drops, eye mist or eye gel, that is, the ophthalmic composition, is an aqueous suspension comprising drug, cyclodextrin and water, the composition having an aqueous phase of from about 0.1 to about 90%, typically about 5 to about 50%, of the drug in solution, as free drug and dissolved drug/cyclodextrin complex(es), and from about 10 to about 99.9%, typically about 50 to about 95%, of the drug as solid drug/cyclodextrin particles. The amount of dissolved drug can be controlled by the ratio of natural cyclodextrin and its water-soluble derivative in the formulation. The size of the particles in the solid phase is from about 10 nm to about 1 mm, typically from about 0.1 to about 500 μm. The drug/cyclodextrin particles are capable of dissolving in the aqueous tear fluid, generally within 24 hours, typically within 10 to 600 minutes, of administration to the eye surface. The particles will be retained on the eye surface and their dissolution will ensure constant high concentration of dissolved drug in the aqueous tear fluid. The resulting high thermodynamic activity of the drug in the tear fluid will enhance drug permeation into the eye. Also, since administration of the cyclodextrin delivery system will result in sustained high drug concentration in the tear fluid, the amount of drug absorbed after each administration will be enhanced. Consequently, since for example 59% of the drug reaching the retina in rabbits gets there via topical route (Experiment 1 below), then enhanced drug delivery into the eye after topical delivery will enhance significantly the drug delivery to the retina and other posterior segments of the eye. This cyclodextrin-based drug delivery system will also enhance drug delivery to the anterior segment of the eye for delivery of, for example, drugs to the aqueous humor resulting in sustained high drug concentrations in the aqueous humor and the anterior segment. There are some additional advantages of this formulation where a large fraction of the drug is in a solid state, including enhanced chemical and physical stability of the drug (that can result in enhanced shelf-life) and reduced cyclodextrin inactivation of added preservatives.

Experiment 2 below shows that topical administration of water-soluble particles to the eye causes negligible irritation.

Experiment 3 below shows that it is possible to enhance topical drug delivery to the eye by increasing the concentration of dissolved drug in the aqueous eye drop solution. However, this will lead to proportional increase in the blood concentration (Table 5) and, consequently, increased possibility (frequency) of systemic side effects.

Experiment 4 below shows that although only about 5% of the drug is in solution, in the aqueous eye drop suspension, significant amounts of the drug are reaching the posterior segment of the eye. Furthermore, drug concentration in blood will remain low (FIG. 3) reducing the likelihood of systemic side effects.

Table 6 shows that the site-specificity of the aqueous drug/cyclodextrin eye drop suspension is significantly greater that that of an aqueous drug/cyclodextrin eye drop solution.

Experiment 5 below relates to microscopic studies of particle size.

Experiment 6 below shows solubilizing effects of cyclodextrins on some drugs.

Experimental Support

Preliminary Experiments

The two most common causes of blindness in developed countries are age-related macular degeneration and diabetic retinopathy. The number of patients with these diseases is increasing rapidly as the number of elderly people and people with diabetes is increasing in the developing countries. Both diabetic retinopathy and age-related macular degeneration are diseases of the retina and the posterior segment of the eye. Old drugs, such as corticosteroids (e.g. triamcinolone and dexamethasone) and new drugs, such as drugs directed against vascular endothelial growth factors and others, show promise in dealing with these diseases but their delivery is very difficult. Traditional eye drops are inadequate in delivering drugs to the posterior segment of the eye. Intravitreal injections are commonly used today. However, these have to be performed in an operating room, involves some risk to the patient and is quite expensive and cumbersome for repeated drug administration. Even when injected into the vitreous, drugs may not have a direct path through the retina to the subretinal space. The same limitations apply to devices implanted in the eye wall for sustained drug release. In this case the drugs flow into the vitreous cavity but will have to cross the retina to reach the subretinal space. Subtenon or extra scleral injections are used and then the drugs have to penetrate the sclera and the choroid to reach the subretinal space and the retina. Finally, systemic administration is possible where the drugs are distributed to all tissues in the body including the retina and optic nerve. The same obstacles are met when glaucoma drugs are used to treat diseases in the optic nerve and retina. These include, for example, carbonic anhydrase inhibitors. Currently, there are no safe and patient-friendly topical drug delivery systems available for effective drug delivery to the posterior segments of the eye. In Experiment 1 a traditional cyclodextrin-containing eye drop solution was used. Randomly methylated β-cyclodextrin, with degree of substitution 1.8, does possess some surface activity and acts as a conventional penetration enhancer increasing drug flow from the surface into the eye by reducing the barrier function of the membrane (i.e. cornea and sclera).

Experiment 1

Aqueous isotonic solution contained 0.5% [1,2,4,6,7-$^3$H]-dexamethasone, 5.3% randomly methylated β-cyclodextrin DS 1.8, benzalkonium chloride (0.02%), EDTA (0.10%), hydroxypropyl methylcellulose (0.10% w/v) and sodium chloride (0.72%), all w/v %. This solution (50 μl) was administered to three groups of rabbits (3×6 rabbits) as eye drops to the left eye only, as nasal spray and as intravenous injection. Blood samples were collected every 30 minutes after drug administration and the rabbits sacrificed after 2 hours. Then both eyes were removed and the dexamethasone concentration determined in blood, cornea, anterior sclera, aqueous humor, lens, iris-ciliary body, vitreous humor, retina, optic nerve and urine, using a liquid scintillation counter. The relative contribution of topical permeation versus systemic delivery was determined by comparing the dexamethasone concentrations in the left and the right eyes after different routes of drug administration.

Results and Conclusions:

Systemic bioavailability after topical administration to the eye (0 to 120 min) was about 60%. The drug reached cornea (98%), anterior slera (93%), aqueous humor (97%) iris-ciliary body (86%) and lens (80%) mainly via permeation from the eye surface. About half of the drug found in vitreous (54%) and retina (59%) appeared to reach these segments via topical permeation, but only about 17% of the drug was found in the optic nerve. Nasal delivery and intravenous injection did not show any advantages over topical drug delivery.

Experiment 2

The purpose of this study was to investigate ocular irritation in rabbits following powder administration.

Methods:

Timolol maleate powder was administered to one eye of each rabbit and the other eye was used as control. Both pure timolol maleate powder and freeze-dried with PVP-polymer (2.4% of mass) were tested in 1.0 mg (n=3) and 0.1 mg (n=6) doses. Additionally, four rabbits received 0.1 mg of the pure powder 3 times a day for 8 days. Redness of bulbar conjunctivae and the amount of discharge were rated from photographs (0-3 points, randomized and masked evaluation). Slitlamp examination was also performed. Hematoxylin-eosin (H&E) stained sections of eyes were examined with a light microscope following the 8 days experiment.

Results:

No serious or irreversible signs of irritation were noted. There was no detectable difference between irritations from pure or freeze-dried powder. The table shows results for pure powder (median and range) (Table 2). Slitlamp examination, surface photographs and histology showed negligible difference between drug and control eyes following 8 days experiment.

Conclusions:

The results suggest that 0.1 mg of timolol powder causes negligible ocular irritation.

TABLE 2

Topical irritation of solid (water-soluble) particles.

| | Bulbar redness (points) | | Discharge (points) | |
|---|---|---|---|---|
| | Drug | Control | Drug | Control |
| 1 hr. after 1.0 mg (n = 3) | 1.0 (1.0-1.5) | 1.0 (1.0-1.0) | 1.0 (0.0-2.0) | 0.3 (0.0-0.3) |
| 24 hr. after 1.0 mg (n = 3) | 1.0 (1.0-1.0) | 1.0 (0.3-1.0) | 0.3 (0.0-0.8) | 0.0 (0.0-0.0) |
| 1 hr. after 0.1 mg (n = 6) | 1.5 (1.0-2.0) | 1.3 (1.0-1.5) | 0.0 (0.0-1.5) | 0.0 (0.0-0.0) |
| 24 hr. after 0.1 mg (n = 6) | 1.0 (0.0-2.0) | 1.0 (0.3-1.5) | 0.0 (0.0-0.0) | 0.0 (0.0-0.0) |
| 0.1 mg × 24 (8 days, n = 4) | 0.8 (0.0-1.5) | 0.3 (0.0-1.3) | 0.0 (0.0-0.5) | 0.0 (0.0-0.0) |

Experiment 3

The purpose of this study was to investigate the concentration of dexamethasone in various eye tissues after topical administration of 0.5 and 1.5% (w/v) dexamethasone solutions containing randomly methylated β-cyclodextrin as solubilizer.

Materials:

[1,2,4,6,7-$^3$H]-dexamethasone in ethanol solution with specific activity of 88 Ci/mmol was purchased from Amersham Biosciences. Dexamethasone was purchased from Sigma (Germany) and Bufa (Netherlands). Randomly methylated β-cyclodextrin with degree of substitution 1.8 (RMβCD) was purchased from Wacker-Chemie GmbH (Germany). Analytical grade of disodium edetate dihydrate (EDTA) was purchased from Merck (Germany). Hydroxypropyl methylcellulose (HPMC) was obtained from Mecobenzon (Denmark). Benzalkonium chloride was purchased from Sigma (USA). Soluene®-350 solubilizer, and liquid scintillation cocktails Hionic Fluor™ and Ultima Gold™ were purchased from Perkin Elmer (UK). All other chemicals used in this study were commercially available compounds of special reagent or analytical grade.

Solubility Studies:

Phase-solubility study was performed to determine the exact amount of RMβCD needed to solubilize dexamethasone in the eye drop medium. An excess amount of dexamethasone was added to aqueous solution containing from 0 to 25% (w/v) RMβCD, benzalkonium chloride (0.02% w/v), EDTA (0.1% w/v), NaCl (0.00 to 0.72% w/v) and HPMC (0.1%). The suspensions formed were heated in an autoclave (Midmark M7 SpeedClave) in sealed containers to 121° C. for 20 min. The suspensions were allowed to cool to room temperature (22-23° C.) and equilibrate for 7 days. After equilibrium was attained, the suspension was filtered through a 0.45 μm membrane filter, diluted and analyzed by HPLC. The phase-solubility diagram of dexamethasone was determined in the aqueous RMβCD (0-25% w/v) eye drop solutions. The phase-solubility was determined to be of $A_L$-type and thus dexamethasone appears to form 1:1 dexamethasone/RMβCD complex in the aqueous eye drop formulation.

Formulation of the Eye Drops:

a) Cold Solution:

Aqueous 0.5 and 1.5% (w/v) dexamethasone eye drop solution was prepared by dissolving 250 or 750 mg of dexamethasone in 45 ml of aqueous solution containing benzalkonium chloride (10 mg), EDTA (50 mg), HPMC (50 mg), NaCl (0 or 360 mg) and RMβCD (2.65 or 9.0 g) and then filled up to 50 ml. The solution was heated in an autoclave (Midmark M7 SpeedClave) in sealed containers to 121° C. for 20 min. The solution was allowed to cool to room temperature (22-23° C.) and equilibrate for 7 days. To prevent drug precipitation during storage 10% excess RMβCD was included in the aqueous eye drop formulation. The osmolarity of the solutions was measured by the freezing point depression method using a Knauer Osmometer Automatic (Netherlands). The viscosity was determined by a Brookfield digital viscometer model DV-1+(U.S.A.) operated at room temperature. The osmolarity of the eye drops was determined to be 284 mOsm/kg. The viscosity was about 2.5 cps.

b) Dosing Solution (Labeled):

The required volume of radioactive dexamethasone ethanolic solution was pipetted in a vial and as much as possible of the ethanol allowed to evaporate almost to dryness without precipitating the dexamethasone. Then, a required amount of dexamethasone eye drop solution was added and that solution was shaken for at least 2 hours.

In Vivo Studies:

Young, unanaesthetized female albino rabbits (HB Lidköbings Kaninfarm, Sweden) were used. The rabbits were fed on a regular diet and weighed about 3 kg. The study adhered to the ARVO declaration for the use of laboratory animals in research. 50 μl of the drug solution was administered via three different routes to three different groups of rabbits (n=6). The drug was administered to one group as an eye drop (topical), intranasally to the second group and intravenously to the third group. Eye drops were instilled using a micropipette inside the center of the lower cul-de sac. During instillation, the lower eyelid was pulled slightly away form the globe and was returned to its normal position immediately after instillation. Great care was taken not to irritate the eye or to touch the corneal surface. Micropipette was used to deliver the dose to the left nostril of the second group. Blood samples were taken at 30 minute intervals. After two hours, the rabbits were sacrificed by intravenous injection of sodium pentobarbital and both eyes were proptosed and enucleated immediately and rinsed with an isotonic saline solution. All solutions were well tolerated by the rabbits and no macroscopic signs of irritation, redness or other toxic effect were observed.

Sample Preparation:

The aqueous humor was removed from the eye using a 1 ml syringe attached to a 26-gauge needle and placed in a polyethylene (scintillation) vial. One lateral incision was performed in the sclera (center of the eyeball) and the eye was totally opened (anterior part and posterior part). From the anterior part, the lens and the iris-ciliary body were removed and the cornea was separated from the remaining anterior sclera. From the posterior part, the vitreous humor was emptied into a vial, the retina was gently scraped away and the optic nerve (about 2 mm) was cut off. While dissecting the eyes, all the samples were immediately put in dry scintillation vials and weighed. Great care was taken to prevent cross-contamination between individual tissue samples and eye fluids. The entire procedure took less than 15 minutes per eye so that any errors due to redistribution of drug were minimized.

Quantitative Determination of Dexamethasone:

a) Aqueous Humor:

10 ml of Ultima gold was added to aqueous humor samples (about 0.2 g), the vials were stoppered, shaken and kept in the dark for at least 12 hours prior to counting in a liquid scintillation counter.

b) Blood Samples:

Blood samples were prepared by adding 1 ml mixture of Soluene®-350:isopropanol to 0.1-0.2 ml of the blood and incubated at 50° C. for 60 minutes. The vials were then allowed to cool down to room temperature and 0.5 ml of 30% hydrogen peroxide solution was then added dropwise with swirling to each vial for decolorization. The solutions were allowed to stand at room temperature for 10 minutes. The vials were then incubated again at 50° C. for 30 minutes to remove excess hydrogen peroxide. After cooling down to room temperature, 10 ml of Hionic Fluor™ was added to each vial which were stoppered, shaken and kept in the dark for at least 12 hours prior to counting in a liquid scintillation counter.

c) Other Ocular Tissue Samples:

Other tissue samples were handled in the same way as the blood samples except that 0.5-2.0 ml of Soluene®-350 was added to the samples depending on the size of the tissue sample. No isopropanol or hydrogen peroxide was used and the samples were incubated for 240 minutes at 50° C. before adding the Hionic Fluor™ (5-20 ml depending on sample size). Dexamethasone was detected in all blood samples and in all tissue samples from the eyes after all three different routes of administration. Blank tissue samples were spiked with various amounts of labeled dexamethasone from the dosing solution and used as a standard.

Results:

Table 3 lists the concentration of dexamethasone after topical application of 0.5% dexamethasone in the left (study) eye and the right (control eye) as well as after intravenous or intranasal application of the same drug dose. After topical application the drug concentration in the left study eye compared to the right control eye is 1187±112 ng/g versus 20±9 ng/g for the cornea, 448±142 ng/g versus 35±14 ng/g for the anterior sclera, 170±76 ng/g versus 6±2 ng/g for the aqueous humor, 136±42 ng/g versus 19±7 ng/g for the iris ciliary body and 11±3 ng/g versus 2±0 ng/g for the lens indicating that topical absorption is very important in the anterior segment of the eye. In the posterior segment the difference between the drug concentrations in the left study eye and the right control eye are less pronounced: 11±3 ng/g versus 5±1 ng/g for the vitreous humor, 33±7 ng/g versus 14±3 ng/g for the retina and 41±12 ng/g versus 34±13 ng/g for the optic nerve (mean±standard deviation, n=6). Increasing the drug concentration in the eye drop solution from 0.5% to 1.5% resulted in over two-fold increase in drug concentration in the posterior segment of the eye, and three to four fold increase in both aqueous humor and iris ciliary body.

The systemic absorption is similar following intravenous, intranasal and topical application of 0.5% solution of the drug. The drug levels in the various ocular tissues are similar in the right control eye following topical application to the left eye, as in each eye following intravenous or intranasal application of the same drug dose. FIG. 1 shows the concentration of dexamethasone in blood. While the pharmacokinetics is different among the topical, intravenous and intranasal application, the concentration of dexamethasone in blood is similar 2 hours after application.

Figure 2:
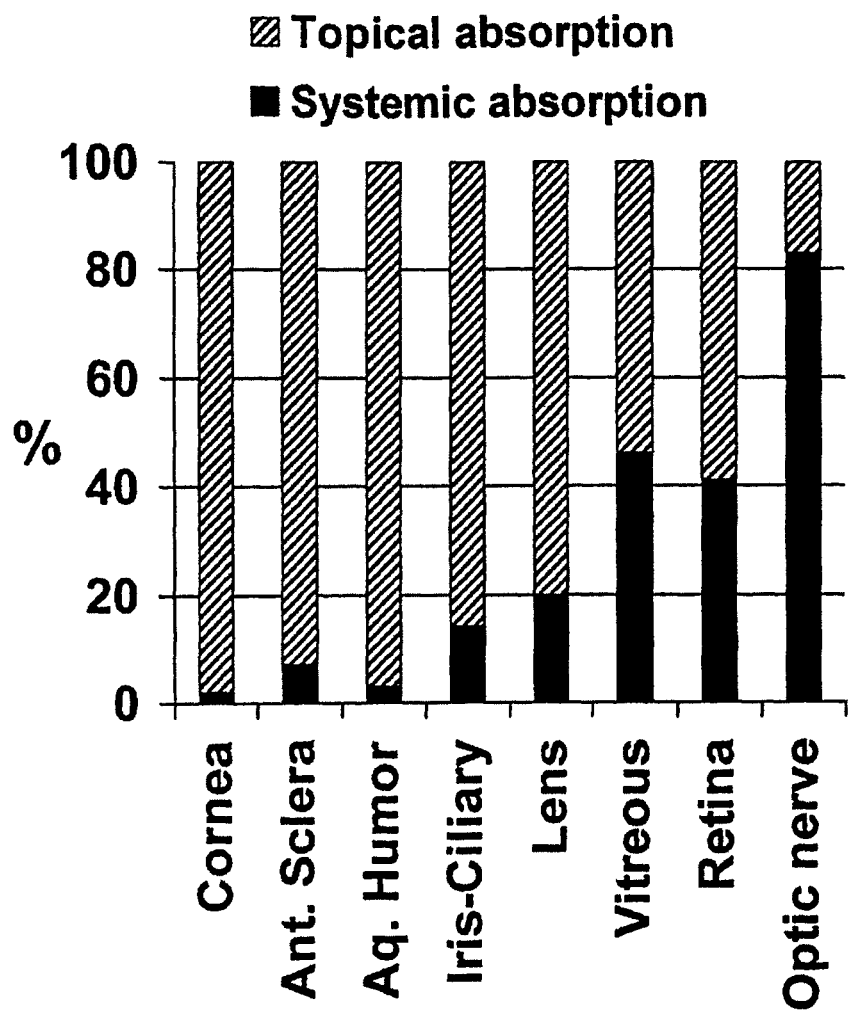
FIG. 2 is a bar graph showing topical and systemic absorption in rabbits in various tissues of the eye after topical administration to the eye of a 0.5% dexamethasone eye drop solution prepared as described in Experiment 1 (prior art randomly methylated β-cyclodextrin/dexamethasone solution).

Discussion:

The experimental design allows comparison of the contribution of topical absorption and systemic absorption to the various ocular tissues by comparing the levels in the study eye and the control eye. FIG. 2 shows the percentage of the drug concentration in each tissue that is delivered by topical absorption or by systemic absorption. As expected, topical absorption dominates in the anterior part of the eye. Topical absorption is also important for drug delivery to the posterior segment and is responsible for more than half of the drug levels in the vitreous and retina following eye drop application in our model. Systemic absorption accounts for about 40% of the drug reaching the posterior part of the eye in this model and topical absorption accounts for 60%. This is a significant finding and in line with the results from Salminen and Urtti for timolol disposition in treated and untreated eye (SALMINEN, L., URTTI, A. (1984) Disposition of ophthalmic timolol in treated and untreated rabbit eyes. A multiple and single dose study. *Experimental Eye Research* 38: 203).

The systemic absorption is roughly the same with topical administration of an eye drop and intranasal and intravenous delivery of the same dose (Table 3). This indicates that the vast majority of the eye drop is absorbed into the blood circulation. The fact that no significant difference in dexamethasone concentration was observed between the left or right eye of the rabbits that received dexamethasone either intranasally or by intravenous injection indicates that the method of sample preparation and the precision of the measurements were very good. The results of this study are also in line with other studies, which report that 50-100% of the instilled dose is absorbed into the systemic circulation. Systemic bioavailability of dexamethasone after topical administration to the eye, determined from the dexamethasone blood concentrations from 0 to 120 min after administration of the drug, was about 60%. This number is probably close to 70-80% when determined from the dexamethasone blood concentrations from 0 to 480 min after administration of the drug, as can be predicted from FIG. 1. Spillage during topical administration will of course always affect those numbers. In general, blood levels should be useful to predict the concentration in the back of the eye. Many factors, such as plasma protein binding and the ability of the drug to transverse the retinal blood barrier, will however influence those predictions.

It is important to note that this experiment was conducted in albino rabbits and not in humans. The contribution of systemic drug return to the ocular tissues would probably be lower in humans since the apparent volume of drug distribution is much greater in 70 kg humans than in 2 kg rabbits. The rabbit eye is smaller than the human and therefore topically absorbed dexamethasone may reach the posterior segment more easily in the rabbit than in man. The volume of the eye drop can also influence the contribution of systemic absorption into the eye.

We have previously demonstrated in human patients that cyclodextrin-based eye drops with a relatively high concentration of dexamethasone penetrate the eye better than commercially available eye drop formulations (KRISTINSSON, J. K., FRIDRIKSDOTTIR, H., THORISDOTTIR, S., SIGURDARDOTTIR, A. M., STEFANSSON, E., LOFTSSON, T. (1996) Dexamethasone-cyclodextrin-polymer co-complexes in aqueous eye drops. Aqueous humor pharmacokinetics in humans. *Investigative Ophthalmology & Visual Science* 37: 1199). The cyclodextrin based 0.5% dexamethasone eye drop delivers significant levels of dexamethasone to the retina and vitreous both through topical and systemic absorption. The drug levels may be further increased by raising the concentration to 1.5% dexamethasone and more frequent application and may present a potential drug delivery platform for treatment of retinal diseases with steroids and other drugs, through a noninvasive route. However, it appears that the increased drug levels in the posterior segment of the eye is mainly due to increased delivery via the systemic route (from the nasal cavity).

TABLE 3

Concentration (ng/g) of dexamethasone in blood and various ocular tissues 120 minutes after administration of 0.5% dexamethasone eye drop solution topically as eye drop, by intravenous injection or by intranasal application of an identical dose in the rabbit, and topical administration of 1.5% dexamethasone eye drop solution (mean ± standard deviation; n = 6).

| | 1.5% w/v Dexamethasone | | 0.5% w/v Dexamethasone | | | | | |
|---|---|---|---|---|---|---|---|---|
| | Topical | | Topical | | Intravenous | | Intranasal | |
| Tissue | Left eye | Right eye | Left eye | Right eye | Left eye | Right eye | Left eye | Right eye |
| Cornea | 1668 ± 633 | 44 ± 44 | 1187 ± 112 | 20 ± 9 | 21 ± 4 | 20 ± 3 | 16 ± 5 | 18 ± 6 |
| Sclera | 231 ± 121 | 31 ± 20 | 448 ± 142 | 35 ± 14 | 28 ± 5 | 26 ± 4 | 21 ± 10 | 25 ± 8 |
| Aqueous Humour | 576 ± 226 | 9 ± 4 | 170 ± 76 | 6 ± 2 | 10 ± 2 | 10 ± 2 | 9 ± 2 | 10 ± 3 |
| Iris-Ciliary body | 548 ± 290 | 43 ± 36 | 136 ± 42 | 19 ± 7 | 15 ± 4 | 19 ± 6 | 19 ± 5 | 19 ± 6 |
| Lens | 19 ± 9 | 5 ± 3 | 11 ± 3 | 2 ± 0 | 3 ± 1 | 3 ± 1 | 3 ± 1 | 3 ± 1 |
| Vitreous | 22 ± 9 | 6 ± 3 | 11 ± 3 | 5 ± 1 | 7 ± 1 | 7 ± 1 | 6 ± 2 | 6 ± 1 |
| Retina | 66 ± 49 | 57 ± 41 | 33 ± 7 | 14 ± 3 | 16 ± 5 | 17 ± 4 | 19 ± 6 | 20 ± 6 |
| Optic nerve | 131 ± 51 | 85 ± 63 | 41 ± 12 | 34 ± 13 | 28 ± 7 | 27 ± 9 | 28 ± 14 | 28 ± 11 |
| Blood | 45 ± 24 | | 26 ± 5 | | 27 ± 4 | | 36 ± 1 | |

The following illustrates, but does not limit, the invention. A representative drug was chosen to illustrate the improved site-specificity of an aqueous cyclodextrin drug suspension as compared to an aqueous cyclodextrin drug solution in targeting delivery to the vitreous, retina and optic nerve following administration to the eye surface.

Experiments Illustrating the Invention

The following experiments are detailed by way of illustration only and are not to be construed as limiting the invention in spirit or in scope as many modifications both in materials and in methods will be apparent to those skilled in the art.

Experiment 4

The purpose of this study was to investigate the concentration of dexamethasone in various eye tissues after topical administration of a dexamethasone suspension containing γ-cyclodextrin.

Materials:

[1,2,4,6,7-$^3$H]-dexamethasone in ethanol solution with specific activity of 88 Ci/mmol was purchased from Amersham Biosciences. Dexamethasone was purchased from Sigma (Germany). γ-Cyclodextrin (γCD) was purchased from Wacker-Chemie GmbH (Germany). Analytical grade of disodium edetate dihydrate (EDTA) was purchased from Norsk Medisinaldepot (Germany). Hydroxypropyl methylcellulose (HPMC) was obtained from Mecobenzon (Denmark). Benzalkonium chloride was purchased from Sigma (USA). Soluene®-350 solubilizer, and liquid scintillation cocktails Hionic Fluor™ and Ultima Gold™ were purchased from Perkin Elmer (UK). All other chemicals used in this study were commercially available compounds of special reagent or analytical grade.

Solubility Studies:

Phase-solubility study was performed to determine the exact amount of γCD needed to solubilize dexamethasone. An excess amount of dexamethasone was added to aqueous solution or suspension containing from 0 to 10% (w/v) γCD. The dexamethasone suspensions formed were heated in an autoclave (Midmark M7 SpeedClave) in sealed containers to 121° C. for 20 min. The suspensions were allowed to cool to room temperature (22-23° C.) and equilibrate for 7 days. After equilibrium was attained, the suspension was filtered through a 0.45 μm membrane filter, and the filtrate diluted and analyzed by HPLC. The phase-solubility diagram in pure water was determined to be of $B_S$-type with a maximum dexamethasone solubility of 5.3 mg/ml at 5% (w/v) γCD concentration.

Formulation of the Eye Drops:

a) Cold Suspension:

Aqueous 1.5% (w/v) dexamethasone eye drop suspension was prepared by suspending 750 mg of dexamethasone in 50 ml of aqueous solution containing benzalkonium chloride (10 mg), EDTA (50 mg), HPMC (50 mg), NaCl (100 mg) and γCD (9.0 g). The suspension was heated in an autoclave (Midmark M7 SpeedClave) in sealed containers to 121° C. for 20 min. The suspension was allowed to cool to room temperature (22-23° C.) and equilibrate for 7 days. The osmolarity of the solutions was measured by the freezing point depression method using a Knauer Osmometer Automatic (Netherlands). The viscosity was determined by a Brookfield digital viscometer model DV-1+ (U.S.A.) operated at room temperature. The osmolarity of the eye drop suspension was determined to be about 300 mOsm/kg (or milliosmolality/kg). The viscosity was about 2.3 cps. The amount of dissolved dexamethasone in the aqueous eye drop suspension was determined to be between 0.7 and 0.9 mg/ml or only about 5% of the total amount of dexamethasone in the eye drop formulation.

b) Dosing Suspension (Labeled):

The required volume of radioactive dexamethasone ethanolic solution was pipetted in a vial and as much as possible of the ethanol allowed to evaporate almost to dryness without precipitating the dexamethasone. Then, a required amount of dexamethasone eye drop suspension was added and that solution was sonicated for 30 minutes and shaken at room temperature for at least 24 hours.

In Vivo Studies:

Eight young, unanaesthetized female albino rabbits (HB Lidköbings Kaninfarm, Sweden) were used. The rabbits were fed on a regular diet and weighed about 3 kg. The study adhered to the ARVO declaration for the use of laboratory animals in research. Eye drops (50 μl) were instilled topically using a micropipette inside the center of the lower cul-de sac (n=8). During instillation, the lower eyelid was pulled slightly away form the globe and was returned to its normal position immediately after instillation. Great care was taken not to irritate the eye or to touch the corneal surface. Blood samples were taken at 30 minute intervals. After two hours, the rabbits were sacrificed by intravenous injection of sodium pentobarbital and both eyes were proptosed and enucleated immediately and rinsed with an isotonic saline solution. All solutions were well tolerated by the rabbits and no macroscopic signs of irritation, redness or other toxic effect were observed.

Sample Preparation:

The aqueous humor was removed from the eye using 1 ml syringe attached to a 26-gauge needle and placed in a polyethylene (scintillation) vial. One lateral incision was performed in the sclera (center of the eyeball) and the eye was totally opened (anterior part and posterior part). From the anterior part, the lens and the iris-ciliary body were removed and the cornea was separated from the remaining anterior sclera. From the posterior part, the vitreous humor was emptied into a vial. The retina was gently scraped away and the optic nerve (about 2 mm) was cut off. While dissecting the eyes, all the samples were immediately put in dry scintillation vials and weighed. Great care was taken to prevent cross-contamination between individual tissue samples and eye fluids. The entire procedure took less than 15 minutes per eye so that any errors due to redistribution of drug were minimized.

Quantitative Determination of Dexamethasone:

a) Aqueous Humor:

10 ml of Ultima gold was added to aqueous humor samples (about 0.2 g), the vials were stoppered, shaken and kept in the dark for at least 12 hours prior to counting in a liquid scintillation counter.

b) Blood Samples:

Blood samples were prepared by adding 1 ml mixture of Soluene®-350:isopronanol to 0.1-0.2 ml of the blood and incubated at 50° C. for 60 minutes. The vials were then allowed to cool down to room temperature and 0.5 ml of 30% hydrogen peroxide solution was then added dropwise with swirling to each vial for decolorization. The solutions were allowed to stand at room temperature for 10 minutes. The vials were then incubated again at 50° C. for 30 minutes to remove excess hydrogen peroxide. After cooling down to room temperature, 10 ml of Hionic Fluor™ was added to each vial, and the vials were stoppered, shaken and kept in the dark for at least 12 hours prior to counting in a liquid scintillation counter.

c) Other Ocular Tissue Samples:

Other tissue samples were handled in the same way as the blood samples except 0.5-2.0 ml of Soluene®-350 was added to the samples depending on the size of the tissue sample. No isopropanol or hydrogen peroxide was used and the samples were incubated for 240 minutes at 50° C. before adding the Hionic Fluor™ (5-20 ml depending on sample size). Dexamethasone was detected in all blood samples and in all tissue samples from the eyes. Blank tissue samples were spiked with various amounts of labeled dexamethasone from the dosing solution and used as a standard.

Figure 3:
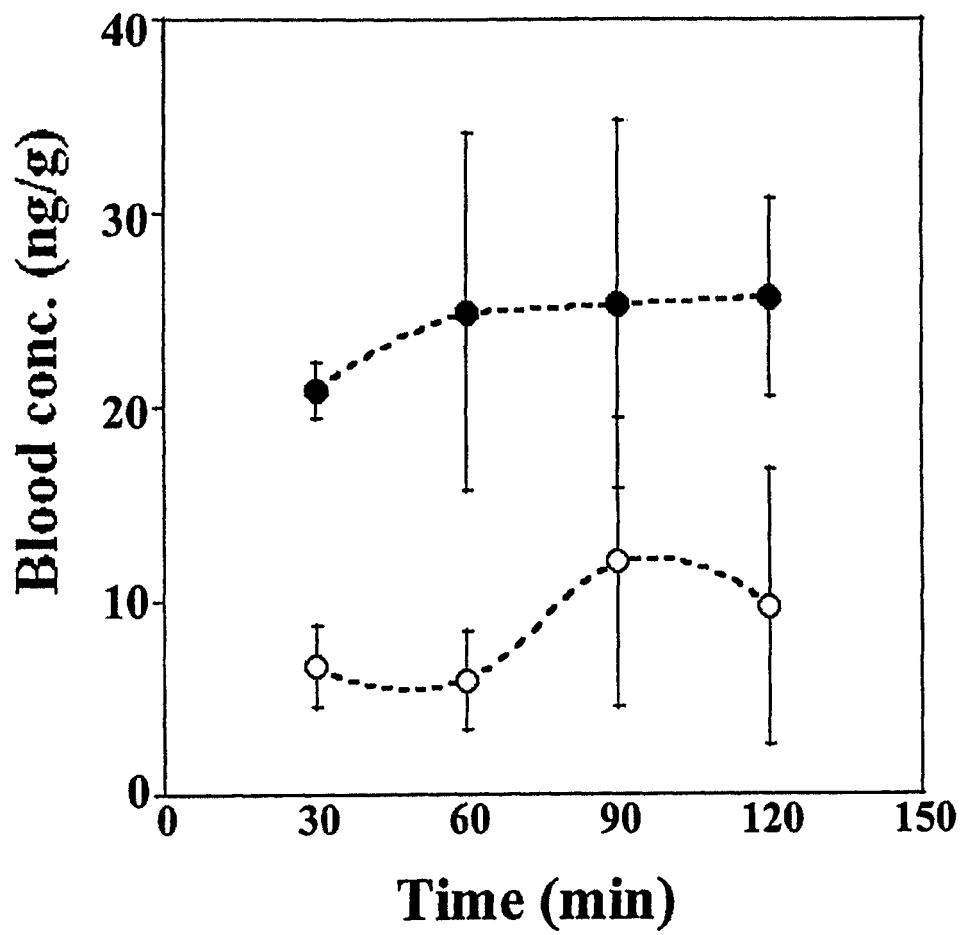
FIG. 3 is a plot of dexamethasone concentrations in blood (in ng/g, mean±standard deviation) against time post treatment, in minutes, after topical administration to the eyes of rabbits of 0.5% dexamethasone/randomly methylated β-cyclodextrin (RMβCD) eye drop solution (prior art solution) (•) or of 1.5% dexamethasone/γ-cyclodextrin (γCD) eye drop suspension (suspension of the invention) (o).
Figure 4:
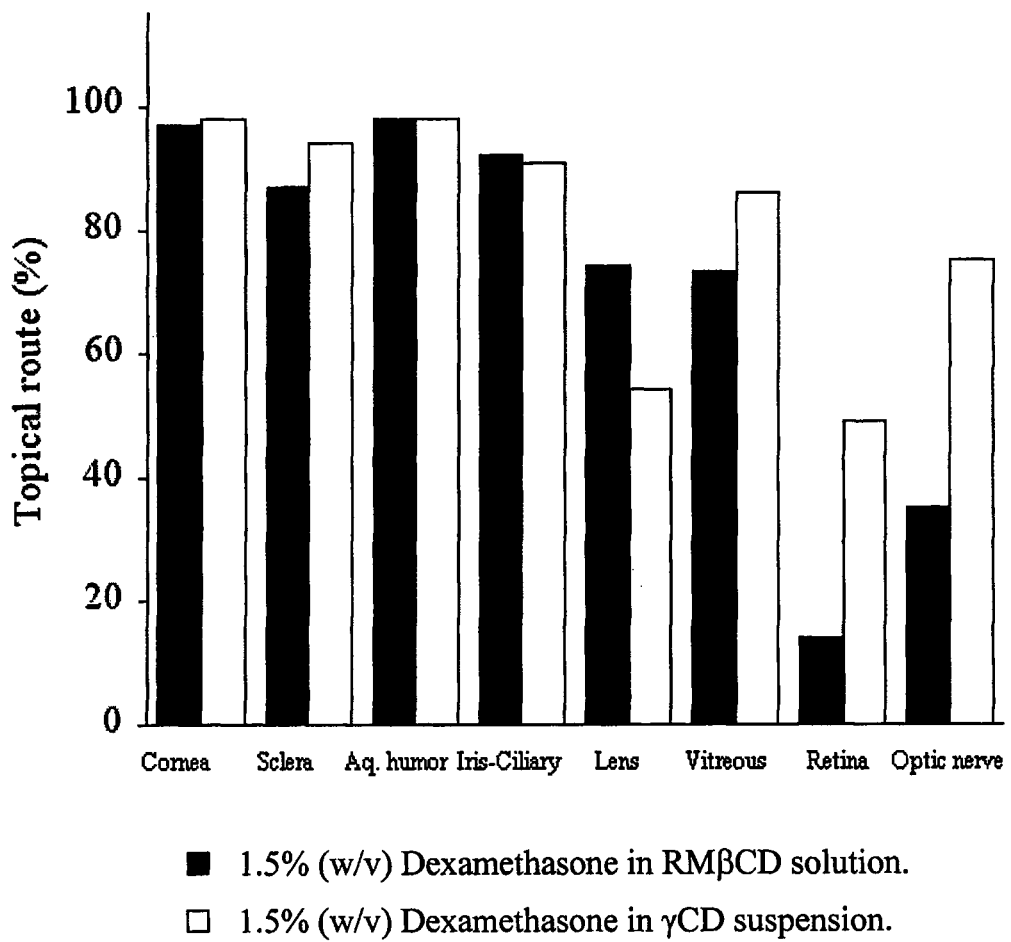
FIG. 4 is a bar graph showing relative amounts of dexamethasone reaching the various eye tissues determined 2 hours after topical administration to the eye of aqueous 1.5% dexamethasone/γ-cyclodextrin eye drop suspension or aqueous 1.5% dexamethasone/randomly methylated β-cyclodextrin eye drop solution to rabbits.

Results:

The results are shown in Table 4. Although the amount of dissolved dexamethasone in the aqueous eye drop suspension was between 0.7 and 0.9 mg/ml, or only about 5% of the total amount of dexamethasone in the eye drop formulation, the dexamethasone amount in the various tissues is comparable or even higher than after administration of the same amount (i.e. 1.5% dexamethasone RMβCD solution) as shown in Table 5. Furthermore, the administration of the dexamethasone/γ-cyclodextrin suspension increases the relative amount of drug reaching the posterior segment of the eye via the topical route and decreases the dexamethasone concentration in blood (FIGS. 3 and 4).

In humans (70 kg) the contribution of the systemic route will be less that 10% of what it is in the much smaller rabbit (3 kg), even when corrected for the relative size of the eyes in the two species. The amount of drug reaching the various tissues via the topical route in the rabbit can be estimated by subtracting the amount of drug in the right eye from the amount of drug in the left eye (Table 6). The amounts shown in Table 6 are closer to what could be expected in humans. Table 6 and the other data presented clearly show that topical administration of aqueous dexamethasone/γ-cyclodextrin eye drop suspension leads to more site-specific drug delivery to the posterior segment of the eye compared to topical administration of aqueous dexamethasone/RMβCD eye drop solution. Thus, this type of formulation not only can enhance drug delivery into the eye after topical drug administration but also decrease systemic side effects.

TABLE 4

Concentration (ng/g) of dexamethasone in blood and various ocular tissues 120 minutes after administration of 1.5% dexamethasone/γ-cyclodextrin eye drop suspension topically as eye drop (mean ± standard deviation; n = 8).

| Tissue | Left eye | Right eye |
|---|---|---|
| Cornea | 1155 ± 324 | 18 ± 12 |
| Sclera | 404 ± 300 | 23 ± 12 |
| Aqueous Humour | 236 ± 67 | 4 ± 2 |
| Iris-Ciliary body | 290 ± 101 | 27 ± 23 |
| Lens | 11 ± 6 | 5 ± 5 |
| Vitreous | 29 ± 16 | 4 ± 4 |
| Retina | 57 ± 22 | 29 ± 15 |
| Optic nerve | 237 ± 152 | 59 ± 40 |
| Blood | 10 ± 7 | |

TABLE 5

Dexamethasone concentration ng/g, mean ± standard deviation) after topical administration to rabbits.

| | 1.5% Dexamethasone γCD suspension | | 1.5% Dexamethasone RMβCD solution | | 0.5% Dexamethasone RMβCD solution | |
|---|---|---|---|---|---|---|
| Tissue | Left eye | Right eye | Left eye | Right eye | Left eye | Right eye |
| Cornea | 1155 ± 324 | 18 ± 12 | 1668 ± 633 | 44 ± 44 | 1187 ± 112 | 20 ± 9 |
| Sclera | 404 ± 300 | 23 ± 12 | 231 ± 121 | 31 ± 20 | 448 ± 142 | 35 ± 14 |
| Aqueous Humour | 236 ± 67 | 4 ± 2 | 576 ± 226 | 9 ± 4 | 170 ± 76 | 6 ± 2 |
| Iris-Ciliary body | 290 ± 101 | 27 ± 23 | 548 ± 290 | 43 ± 36 | 136 ± 42 | 19 ± 7 |
| Lens | 11 ± 6 | 5 ± 5 | 19 ± 9 | 5 ± 3 | 11 ± 3 | 2 ± 0 |
| Vitreous | 29 ± 16 | 4 ± 4 | 22 ± 9 | 6 ± 3 | 11 ± 3 | 5 ± 1 |
| Retina | 57 ± 22 | 29 ± 15 | 66 ± 49 | 57 ± 41 | 33 ± 7 | 14 ± 3 |
| Optic nerve | 237 ± 152 | 59 ± 40 | 131 ± 51 | 85 ± 63 | 41 ± 12 | 34 ± 13 |
| Blood | 10 ± 7 | | 45 ± 24 | | 26 ± 5 | |

TABLE 6

Dexamethasone concentration (ng/g, mean ± standard deviation) reaching the various eye tissues via the topical route after topical administration.

| | Dexamethasone concentration reaching the eye tissue (left eye) via topical route (ng/g) | |
|---|---|---|
| Tissue | 1.5% in γCD suspension | 1.5% in RMβCD solution |
| Cornea | 1137 | 1624 |
| Sclera | 381 | 200 |
| Aqueous Humour | 232 | 567 |
| Iris-Ciliary body | 263 | 505 |
| Lens | 6 | 14 |
| Vitreous | 25 | 16 |
| Retina | 28 | 9 |
| Optic nerve | 178 | 46 |

Experiment 5

The purpose of this study was to determine the size of the particles in representative aqueous eye drop suspensions of the invention and to compare the results with a similar study of prior art aqueous eye drop solutions.

Materials:

Aqueous dexamethasone/γCD eye drop suspension containing 1.5% (w/v) dexamethasone freshly prepared as described in EXPERIMENT 4 above; aqueous dexamethasone/RMβCD eye drop solutions containing 0.5% (w/v) and 1.5% (w/v) dexamethasone, respectively, prepared as described in EXPERIMENT 3 above, freshly prepared; aqueous dexamethasone/γCD eye drop suspension containing 1.5% (w/v) dexamethasone, prepared as described in EXPERIMENT 4 above, then stored at room temperature for 7 months; and aqueous dexamethasone/RMβCD eye drop solutions containing 0.5% and 1.5% (w/v) dexamethasone, respectively, prepared as described in EXPERIMENT 3 above, then stored at room temperature for 7 months.

Figure 5:
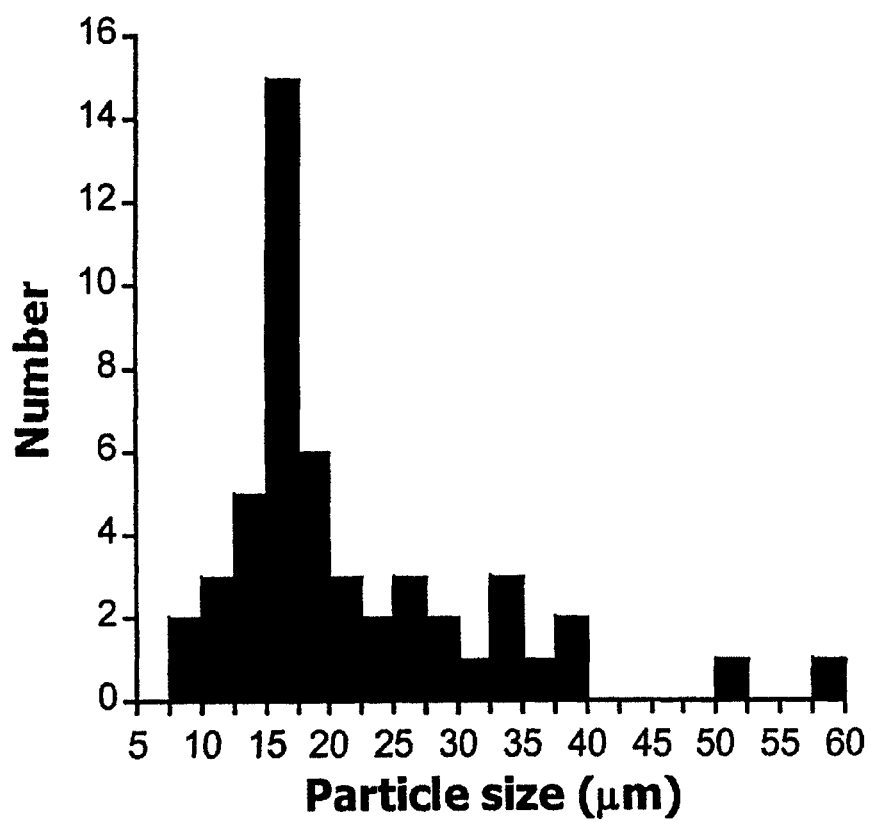
FIG. 5 is a bar graph showing the distribution of particle size in aqueous 1.5% dexamethasone/γ-cyclodextrin (γ CD) eye drop suspension (suspension of the invention), freshly prepared, for a representative 50 particles.
Figure 6:
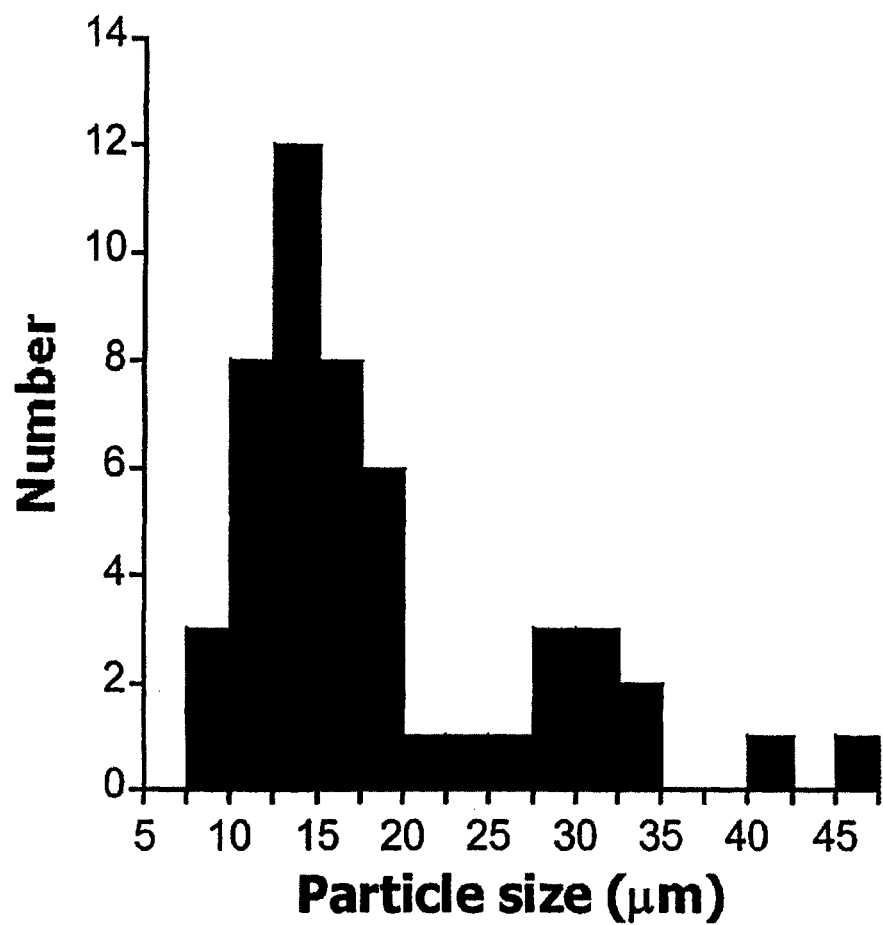
FIG. 6 is a bar graph showing the distribution of particle size in aqueous 1.5% dexamethasone/γ-cyclodextrin (γ CD) eye drop suspension (suspension of the invention), after storage for 7 months, for a representative 50 particles.

Microscopic Study of Particles:

The method described in the European Pharmacopoeia, Edition 5.3, Section 2.9.37, Optical Microscopy (January 2006: 20937) was used. Briefly, the samples were examined in an Olympus BH-2 microscope under 40-fold magnification. The aqueous eye drop formulations were shaken and then one small drop of each was placed on a glass microscope slide and the drop covered by a glass coverslip. Then 50 particles were measured at random by measuring the maximum diameter of particles positioned on straight lines across the sample. In other words, the size of the particles is reported as the longest dimension from edge to edge when the particle is orientated parallel to the ocular scale (as described in the European Pharmacopoeia). The largest particles seen in the freshly prepared aqueous dexamethasone/γCD eye drop suspension were about 60 μm in diameter (i.e. the longest diameter), but the most common size was approximately 15 μm in diameter; N=50, mean±standard deviation=20.35±10.31 μm; see the results shown in FIG. 5. In the aqueous dexamethasone/γCD suspension which had been stored for 7 months at room temperature, the largest particles were about 50 μm in diameter, with the most common size being approximately 12 μm in diameter; N=50, mean±standard deviation=17.35±8.65 μm. See the results shown in FIG. 6. In contrast, no particles were observed under the same conditions in the dexamethasone/RMβCD eye drop solutions.

Experiment 6

Figure 7:
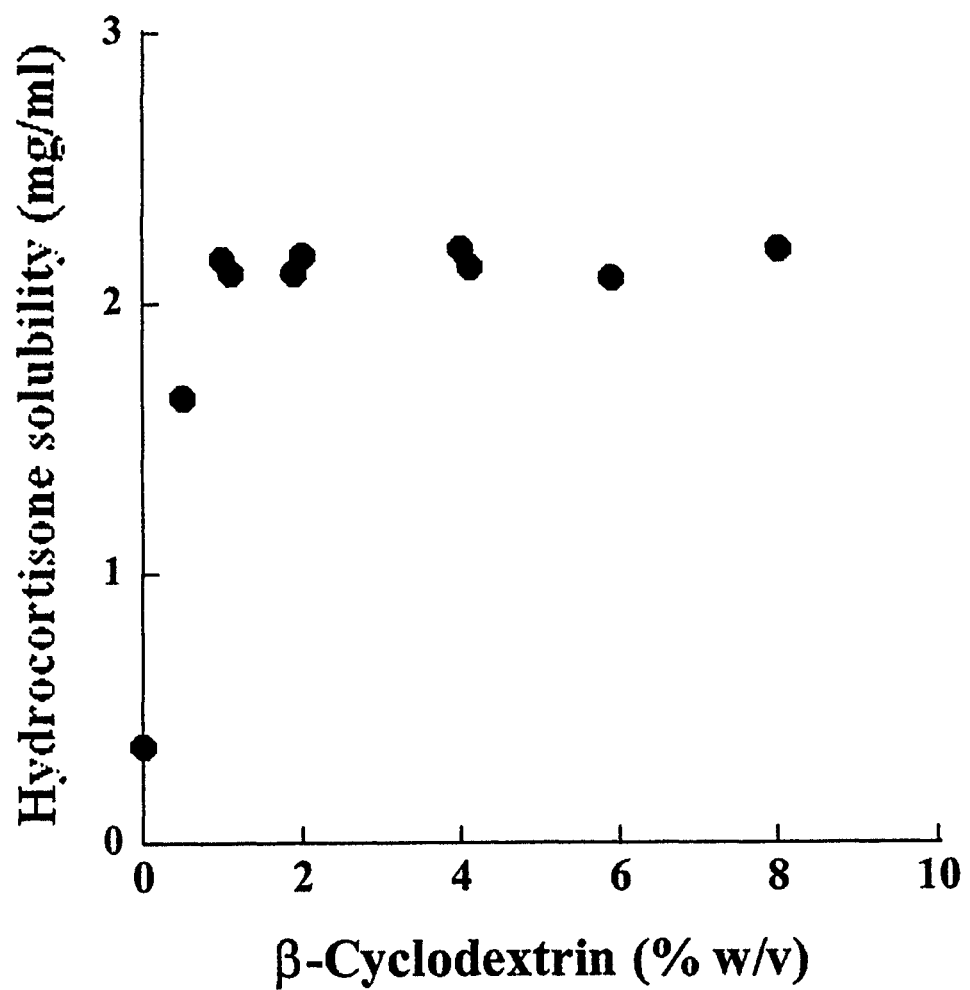
FIG. 7 is a phase-solubility diagram of hydrocortisone in pure aqueous β-cyclodextrin solution or suspension (depending on the concentration) at room temperature.

The solubility of various drugs was determined in pure aqueous solutions containing the natural cyclodextrins or their water-soluble derivatives at room temperature (22-23° C.). The cyclodextrin concentrations, given in parentheses, are weight/volume % and the drug solubilities are in mg/ml. The method used to determine the solubilities has been described (see T. Loftsson, D. Hreinsdóttir and M. Masson, "Evaluation of cyclodextrin solubilization of drugs", *Int. J. Pharm.* 302, 18-28, 2005). The phase-solubilities of drugs in aqueous solutions containing the natural α-, β- or γ-cyclodextrins are, in general, of $B_s$-type, meaning that the drug/cyclodextrin complex has limited solubility in water. At concentrations above the solubility of the drug/cyclodextrin complex only a fraction of the drug will be in solution as drug/cyclodextrin complex and a fraction of the drug will be present as drug/cyclodextrin solid particles in suspension. All three natural cyclodextrins, that is α-, β- and γ-cyclodextrin, form $B_s$-type phase-solubility diagrams while the more water-soluble cyclodextrin derivatives, such as 2-hydroxypropyl-β-cyclodextrin and sulfobutyl ether β-cyclodextrin, do in general form water-soluble complexes or complexes that have much greater water-solubility than complexes of the same drugs with α-, β- and γ-cyclodextrin. FIG. 7 shows the phase-solubility of hydrocortisone in water containing the natural β-cyclodextrin. The maximum hydrocortisone solubility obtained is 2.2 mg/ml and it will not increase with increasing amount of cyclodextrin. On the contrary it will, at certain cyclodextrin concentration, decrease with increasing amount of β-cyclodextrin (which is characteristic for phase-solubility profiles of $B_s$-type). In the case of dexamethasone in pure water containing γ-cyclodextrin the maximum solubility was determined to be 5.3 mg/ml. The solubility of dexamethasone in aqueous eye drop formulation containing 18% γ-cyclodextrin was determined to be 0.7 to 0.9 mg/ml (see EXPERIMENT 4). The aqueous complexation media for hydrocortisone is a solution at β-cyclodextrin concentrations below about 1.8% but a suspension at higher β-cyclodextrin concentrations.

Results:
AG013958 (VEGFR/PDGFR Inhibitor):
γ-cyclodextrin: 0.01 mg/ml (7.5%), 0.02 mg/ml (15%).
Randomly methylated β-cyclodextrin: 0.2 mg/ml (10%)
Sulfobutyl ether β-cyclodextrin: 0.05 mg/ml (10%)
2-Hydroxypropyl-β-cyclodextrin: 0.04 mg/ml (10%)
Carvedilol (Beta Blocker):
α-cyclodextrin: 0.10 mg/ml (10%), 0.13 mg/ml (20%).
β-cyclodextrin: 0.45 mg/ml (10%), 0.9 mg/ml (20%).
γ-cyclodextrin: 0.85 mg/ml (10%), 0.9 mg/ml (20%).
Randomly methylated β-cyclodextrin: 0.5 mg/ml (5%)
Sulfobutyl ether β-cyclodextrin: 0.4 mg/ml (5%)
2-Hydroxypropyl-β-cyclodextrin: 0.3 mg/ml (5%)
Cyclosporine A (Immunosuppressant):
α-cyclodextrin: 0.2 mg/ml (5%), 0.9 mg/ml (10%).
2-Hydroxypropyl-α-cyclodextrin: 0.5 mg/ml (15%)
2-Hydroxypropyl-β-cyclodextrin: 0.2 mg/ml (10%)
Randomly methylated β-cyclodextrin: 0.4 mg/ml (10%)
Dexamethasone (Corticosteroid):
γ-cyclodextrin: 3 mg/ml (5%)
Randomly methylated β-cyclodextrin: 5 mg/ml (5%)
2-Hydroxypropyl-β-cyclodextrin: 4 mg/ml (5%)
17β-Estradiol (Estrogen):
γ-cyclodextrin: 0.4 mg/ml (5%)
Randomly methylated β-cyclodextrin: 4 mg/ml (5%)
2-Hydroxypropyl-γ-cyclodextrin: 2.5 mg/ml (10%)
2-Hydroxypropyl-β-cyclodextrin: 2.4 mg/ml (5%), 4.6 mg/ml (10%), 9.6 mg/ml (20%)
Hydrocortisone (Corticosteroid):
γ-cyclodextrin: 3.6 mg/ml (5%)
Randomly methylated β-cyclodextrin: 11 mg/ml (5%)
2-Hydroxypropyl-α-cyclodextrin: 2.4 mg/ml (5%)
2-Hydroxypropyl-β-cyclodextrin: 6.7 mg/ml (5%)
2-Hydroxypropyl-γ-cyclodextrin: 7.7 mg/ml (5%)
Oxazepam (Benzodiazepine):
γ-cyclodextrin: 0.3 mg/ml (5%)
Randomly methylated β-cyclodextrin: 0.9 mg/ml (5%)
2-Hydroxypropyl-β-cyclodextrin: 1 mg/ml (5%)
Sulfamethoxazole (Sulfonamide):
γ-cyclodextrin: 2.2 mg/ml (5%)
2-Hydroxypropyl-β-cyclodextrin: 6.8 mg/ml (5%)
Triamcinolone Acetonide (Corticosteroid):
γ-cyclodextrin: 4.4 mg/ml (5%)
Randomly methylated β-cyclodextrin: 2.0 mg/ml (5%)
Sulfobutyl ether β-cyclodextrin: 1.1 mg/ml (5%)
2-Hydroxypropyl-β-cyclodextrin: 1.0 mg/ml (5%)

Due to the $B_s$-type of the phase-solubility diagrams of the natural cyclodextrins the drugs will form drug/cyclodextrin suspensions in the aqueous eye drop formulations. The suspensions will partly dissolve upon topical administration to the eye forming a saturated drug solution in the aqueous tear fluid, maximizing the amount of drug partitioning into cornea, slera and other surface tissues. The high chemical potential of the drug in a saturated solution will increase the chemical potential gradient which is the driving force of passive diffusion.

Drug solubility in the aqueous eye drop formulation and/or the tear fluid can be adjusted by simultaneous usage of a natural cyclodextrin and a more water-soluble cyclodextrin derivative.

Experiment 7

A human study is planned to find the level of dexamethasone delivered to the back of the human eye by an eye drop suspension containing dexamethasone-cyclodextrin particles prepared in accord with the invention. Patients who are planning to undergo vitreous surgery will be recruited for the study by informed consent. They will receive one drop of the eye drop suspension at 1, 2 and 4 hours prior to surgery. During surgery, a small sample of the vitreous gel (which is removed routinely in vitreous surgery) will be obtained and stored for dexamethasone measurement.

Embodiments

The following represent particular embodiments of the invention described herein.

1. An ophthalmic composition which is an aqueous suspension comprising drug, cyclodextrin and water, the composition having an aqueous phase of from about 0.1% (w/v) to about 90% (w/v) of the drug in solution, as dissolved free drug and as dissolved drug/cyclodextrin complex(es), and a solid phase of from about 10% (w/v) to about 99.9% (w/v) of the drug as solid drug/cyclodextrin particles, the size of the particles in the solid phase being from about 10 nm to about 1 mm, the drug/cyclodextrin particles being capable of dissolving in tear fluid within about 24 hours after application to the eye surface.

2. The composition according to embodiment 1, in the form of eye drops.

3. The composition according to embodiment 1, in the form of an eye mist or an eye gel.

4. The composition according to embodiment 1, 2 or 3, comprising from about 0.25% to about 40% of cyclodextrin.
5. The composition according to embodiment 4, comprising from about 2% (w/v) to about 20% (w/v) of cyclodextrin.
6. The composition according to any one of the preceding embodiments, further comprising up to about 5% (w/v) of water-soluble polymer.
7. The composition according to embodiment 6, comprising from about 0.1% (w/v) to about 1% (w/v) of water-soluble polymer.
8. The composition according to any one of the preceding embodiments, further comprising up to about 5% (w/v) of metal salts.
9. The composition according to embodiment 8, comprising up to about 2% (w/v) of metal salts.
10. The composition according to any one of the preceding embodiments, further comprising up to about 5% (w/v) of organic salts.
11. The composition according to embodiment 10, comprising up to about 3% (w/v) of organic salts.
12. The composition according to any one of the preceding embodiments, further comprising at least one buffer salt and/or at least one preservative.
13. The composition according to any one of the preceding embodiments, wherein the aqueous phase comprises from about 5% (w/v) to about 50% (w/v) of the drug in solution, as free drug and dissolved drug/cyclodextrin complex(es), and from about 50% (w/v) to about 95% (w/v) of the drug as solid drug/cyclodextrin particles.
14. The composition according to any one of the preceding embodiments, wherein the size of the particles in the solid phase is from about 0.1 μm to about 500 μm.
15. The composition according to any one of the preceding embodiments, wherein the drug/cyclodextrin particles dissolve within from about 10 to about 600 minutes after administration to the eye surface.
16. The composition according to any one of the preceding embodiments, wherein the cyclodextrin comprises at least one natural cyclodextrin selected from the group consisting of α-cyclodextrin, β-cyclodextrin and γ-cyclodextrin.
17. The composition according to any one of embodiments 1-15, comprising at least one pharmaceutically acceptable derivative of α-, β- or γ-cyclodextrin.
18. The composition according to embodiment 17, wherein the at least one pharmaceutically acceptable derivative is selected from the group consisting of hydroxyalkyl-β-cyclodextrins, hydroxyalkyl-γ-cyclodextrins, randomly methylated β-cyclodextrin, β-cyclodextrin sulfobutyl ether, γ-cyclodextrin sulfobutyl ether, branched β-cyclodextrins and branched γ-cyclodextrins.
19. The composition according to embodiment 18, wherein the at least one pharmaceutically acceptable derivative is hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin.
20. The composition according to embodiment 16, wherein the cyclodextrin comprises at least γ-cyclodextrin.
21. The composition according to embodiment 17, wherein the cyclodextrin comprises at least hydroxypropyl-γ-cyclodextrin.
22. The composition according to embodiment 6, wherein said polymer is a cellulose derivative.
23. The composition according to embodiment 6, wherein said polymer is a mucoadhesive water-soluble polymer.
24. The composition according to embodiment 6, wherein said polymer is methylcellulose, hydroxyethyl cellulose, hydroxypropyl cellulose, hydroxypropyl methylcellulose, hydroxypropyl ethylcellulose, carboxymethylcellulose, polyvinyl alcohol, poly(methyl methacrylate), polycarbophil, gelatin, alginate, poly(acrylic acid), polyvinylpyrrolidone, polyethylene glycol, polyethylene oxide or chitosan, or a derivative of one of the foregoing.
25. The composition according to embodiment 8, wherein said metal salt has a divalent or trivalent cation.
26. The composition according to embodiment 25, wherein said metal salt is a magnesium salt.
27. The composition according to embodiment 26, wherein said magnesium salt is magnesium chloride.
28. The composition according to embodiment 10, wherein said organic salt is a salt of or the ionized form of acetic acid, glutaric acid, a hydroxy acid or an amino acid.
29. The composition according to embodiment 28, wherein said organic salt is a salt of or the ionized form of citric acid, lactic acid, ascorbic acid, tartaric acid or lysine.
30. The composition according to embodiment 1, wherein said drug is a carbonic anhydrase inhibitor.
31. The composition according to embodiment 30, wherein said carbonic anhydrase inhibitor is dorzolamide, acetazolamide, methazolamide, ethoxyzolamide or brinzolamide.
32. The composition according to embodiment 1, wherein said drug is a steroid.
33. The composition according to embodiment 32, wherein said steroid is dexamethasone, hydrocortisone, triamcinolone, triamcinolone acetonide, prednisolone, fluorometholone, medrysone, rimexolone, pregnanolone, loteprednol etabonate or etiprednol dicloacetate.
34. The composition according to embodiment 1, wherein said drug is a GABAergic drug.
35. The composition according to embodiment 34, wherein said GABAergic drug is baclofen, tiagabine, valproic acid, progabide, muscimol, etomidate or propofol.
36. The composition according to embodiment 34, wherein said GABAergic drug is a benzodiazepine.
37. The composition according to embodiment 36, wherein the benzodiazepine is diazepam, alprazolam, brotizolam, chlordiazepoxide, clobazam, clonazepam, clorazepam, demoxazepam, flumazenil, flurazepam, halazepam, midazolam, nordazepam, medazepam, nitrazepam, oxazepam, medazepam, lorazepam, prazepam, quazepam, triazolam, temezepam or lorazolam.
38. The composition according to embodiment 1, wherein said drug is a non-steroidal antiinflammatory drug.
39. The composition according to embodiment 38, wherein the non-steroidal anti-inflammatory drug is naproxen or ketoprofen.
40. The composition according to embodiment 1, wherein said drug is an antibiotic.
41. The composition according to embodiment 1, wherein said drug is an antiviral agent.
42. The composition according to embodiment 1, wherein said drug is cyclosporin A.
43. The composition according to embodiment 1, wherein said drug is a prostaglandin.
44. The composition according to embodiment 43, wherein the prostaglandin is latanoprost.
45. A nasal composition which is an aqueous suspension comprising drug, cyclodextrin and water, the composition having an aqueous phase of from about 1% (w/v) to about 95% (w/v) of the drug in solution, as dissolved free drug and as dissolved drug/cyclodextrin complex(es), and a solid phase of from about 5% (w/v) to about 99% (w/v) of the drug as solid drug/cyclodextrin particles, the size of the particles in the solid phase being from about 10 nm to about 1 mm, the drug/cyclodextrin particles being capable of dissolving in nasal mucus fluid within about 24 hours after application to the nasal mucosa.

46. The composition according to embodiment 45, in the form of nose drops.

47. The composition according to embodiment 45, in the form of a nasal mist or a nasal gel.

48. The composition according to embodiment 45, 46 or 47, comprising from about 0.25% to about 45% of cyclodextrin.

49. The composition according to embodiment 48, comprising from about 2% (w/v) to about 25% (w/v) of cyclodextrin.

50. The composition according to any one of embodiments 45-49, further comprising up to about 5% (w/v) of water-soluble polymer.

51. The composition according to embodiment 50, comprising from about 0.1% (w/v) to about 1% (w/v) of water-soluble polymer.

52. The composition according to any one of embodiments 45-51, further comprising up to about 5% (w/v) of metal salts.

53. The composition according to embodiment 52, comprising up to about 2% (w/v) of metal salts.

54. The composition according to any one of embodiments 45-53, further comprising up to about 5% (w/v) of organic salts.

55. The composition according to embodiment 54, comprising up to about 3% (w/v) of organic salts.

56. The composition according to any one of embodiments 45-55, further comprising at least one buffer salt and/or at least one preservative.

57. The composition according to any one of embodiments 45-56, wherein the aqueous phase comprises from about 10% (w/v) to about 50% (w/v) of the drug in solution, as free drug and dissolved drug/cyclodextrin complex(es), and from about 50% (w/v) to about 90% (w/v) of the drug as solid drug/cyclodextrin particles.

58. The composition according to any one of embodiments 45-57, wherein the size of the particles in the solid phase is from about 0.1 µm to about 500 µm.

59. The composition according to any one of embodiments 45-58, wherein the drug/cyclodextrin particles dissolve within from about 10 to about 600 minutes after administration to the nasal mucosa.

60. The composition according to any one of embodiments 45-59, wherein the cyclodextrin comprises at least one natural cyclodextrin selected from the group consisting of α-cyclodextrin, β-cyclodextrin and γ-cyclodextrin.

61. The composition according to embodiment 60, further comprising at least one pharmaceutically acceptable derivative of α-, β- or γ-cyclodextrin.

62. The composition according to embodiment 61, wherein the at least one pharmaceutically acceptable derivative is selected from the group consisting of hydroxyalkyl-β-cyclodextrins, hydroxyalkyl-γ-cyclodextrins, randomly methylated β-cyclodextrin, β-cyclodextrin sulfobutyl ether, γ-cyclodextrin sulfobutyl ether, branched β-cyclodextrins and branched γ-cyclodextrins.

63. The composition according to embodiment 62, wherein the at least one pharmaceutically acceptable derivative is hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin.

64. The composition according to embodiment 60, wherein the cyclodextrin comprises at least γ-cyclodextrin.

65. The composition according to embodiment 64, wherein the cyclodextrin comprises at least hydroxypropyl-γ-cyclodextrin.

66. The composition according to embodiment 50, wherein said polymer is a cellulose derivative.

67. The composition according to embodiment 50, wherein said polymer is a mucoadhesive water-soluble polymer.

68. The composition according to embodiment 50, wherein said polymer is methylcellulose, hydroxyethyl cellulose, hydroxypropyl cellulose, hydroxypropyl methylcellulose, hydroxypropyl ethylcellulose, carboxymethylcellulose, polyvinyl alcohol, poly(methyl methacrylate), polycarbophil, gelatin, alginate, poly(acrylic acid), polyvinylpyrrolidone, polyethylene glycol, polyethylene oxide or chitosan, or a derivative of one of the foregoing.

69. The composition according to embodiment 52, wherein said metal salt has a divalent or trivalent cation.

70. The composition according to embodiment 69, wherein said metal salt is a magnesium salt.

71. The composition according to embodiment 70, wherein said magnesium salt is magnesium chloride.

72. The composition according to embodiment 54, wherein said organic salt is a salt of or the ionized form of acetic acid, glutaric acid, a hydroxy acid or an amino acid.

73. The composition according to embodiment 72, wherein said organic salt is a salt of or the ionized form of citric acid, lactic acid, ascorbic acid, tartaric acid or lysine.

74. The composition according to embodiment 45, wherein said drug is a steroid.

75. The composition according to embodiment 74, wherein said steroid is dexamethasone, hydrocortisone, triamcinolone, triamcinolone acetonide, prednisolone, fluorometholone, medrysone, rimexolone, pregnanolone, loteprednol etabonate or etiprednol dicloacetate.

76. The composition according to embodiment 45, wherein said drug is an anti-migraine drug.

77. The composition according to embodiment 76, wherein said anti-migraine drug is pizotifen, clonidine or sumatriptan.

78. The composition according to embodiment 45, wherein said drug is a narcotic analgesic.

79. The composition according to embodiment 78, wherein said narcotic analgesic is fentanyl or morphine.

80. The composition according to embodiment 45, wherein said drug is propofol, ketamine, scopolamine, etomidate, nicotine, estradiol or testosterone.

81. The composition according to embodiment 45, wherein said drug is a GABAergic drug.

82. The composition according to embodiment 81, wherein said GABAergic drug is a benzodiazepine.

83. The composition according to embodiment 82, wherein the benzodiazepine is diazepam, alprazolam, brotizolam, chlordiazepoxide, clobazam, clonazepam, clorazepam, demoxazepam, flumazenil, flurazepam, halazepam, midazolam, nordazepam, medazepam, nitrazepam, oxazepam, medazepam, lorazepam, prazepam, quazepam, triazolam, temezepam or lorazolam.

84. An ophthalmic composition which is a powder obtained by drying an aqueous suspension as defined in any one of embodiments 1, and 4-44.

85. The composition according to embodiment 84, obtained by lyophilizing or spray-drying said aqueous suspension.

86. The composition according to embodiment 1, wherein said cyclodextrin is a mixture of a natural α-, β- or γ-cyclodextrin and the corresponding water-soluble α-, β- or γ-cyclodextrin derivative.

87. The composition according to embodiment 86, wherein said water-soluble derivative is selected from the group consisting of hydroxyalkyl-β-cyclodextrins, hydroxyalkyl-γ-cyclodextrins, randomly methylated β-cyclodextrin, the sulfobutyl ether of β-cyclodextrin, the sulfobutyl ether of γ-cyclodextrin, branched β-cyclodextrins and branched γ-cyclodextrins.

88. The composition according to embodiment 87, wherein said water-soluble derivative is selected from the group consisting of hydroxypropyl-β-cyclodextrin, hydroxypropyl-γ-cyclodextrin, randomly methylated β-cyclodextrin, the sulfobutyl ether of β-cyclodextrin, the sulfobutyl ether of γ-cyclodextrin, glucosyl β-cyclodextrin and glucosyl γ-cyclodextrin.

89. The composition according to embodiment 86, wherein said cyclodextrin is a mixture of γ-cyclodextrin and 2-hydroxypropyl-γ-cyclodextrin.

90. The composition according to embodiment 86, wherein said cyclodextrin is a mixture of γ-cyclodextrin and the sulfobutyl ether of γ-cyclodextrin.

91. The composition according to embodiment 86, wherein said cyclodextrin is a mixture of β-cyclodextrin and 2-hydroxypropyl-β-cyclodextrin.

92. The composition according to embodiment 86, wherein said cyclodextrin is a mixture of β-cyclodextrin and the sulfobutyl ether of β-cyclodextrin.

93. The composition according to embodiment 86, wherein said cyclodextrin is a mixture of β-cyclodextrin and randomly methylated β-cyclodextrin.

94. A method for the treatment of a condition of the posterior segment and/or the anterior segment of the eye comprising applying topically to the eye surface of a subject in need of such treatment, in an amount which delivers to said segment or segments a therapeutically effective amount of a drug suitable for treating said condition, an ophthalmic composition according to embodiment 1.

95. A method according to embodiment 94, wherein the drug is a corticosteroid and the condition is a disease of the retina and/or optic nerve which is responsive to treatment with a corticosteroid.

96. A method according to embodiment 94, wherein the drug is a carbonic anhydrase inhibitor and the condition is a disease of the retina and/or optic nerve which is responsive to treatment with a carbonic anhydrase inhibitor.

97. A method according to embodiment 94, wherein the drug is a GABA agonist and the condition is a disease of the retina which is responsive to treatment with a GABA agonist.

98. A method according to embodiment 94, wherein the condition is age-related macular degeneration and the drug is AG013958, triamcinolone acetonide, ranibizumab, macugen or sham.

99. The composition according to embodiment 1, wherein the drug is AG013958, triamcinolone acetonide, ranibizumab, macugen or sham.

100. The composition according to embodiment 99, in the form of eye drops.

101. The solid ophthalmic formulation according to embodiment 84, wherein said drug is AG013958, triamcinolone acetonide, ranibizumab, macugen or sham.

Although the invention has been described in some detail by way of illustration and experiments and preferred embodiments, for purposes of clarity of understanding, it will be appreciated by one of ordinary skill that various modifications, substitutions, omissions and additions may be made without departing from the spirit thereof. Accordingly, it is intended that the scope of the present invention be limited solely by the scope of the following claims.

What is claimed is:

1. A method for enhanced delivery of an ophthalmically active drug to the posterior segment of the eye, said method comprising applying topically to the eye surface of a subject in need of such delivery, an ophthalmic composition which is an aqueous suspension comprising drug, cyclodextrin and water, the drug having a solubility in pure water of less than 1 mg/ml at physiologic pH, the composition having an aqueous phase of from about 5% (w/v) to about 50% (w/v) of the drug in solution, as dissolved free drug and as dissolved drug/cyclodextrin complex(es), and a solid phase of from about 50% (w/v) to about 95% (w/v) of the drug as solid drug/cyclodextrin complex particles, the size of the particles in the solid phase being from about 0.1 μm to about 500 μm, the drug/cyclodextrin complex particles being capable of dissolving in tear fluid, the cyclodextrin comprising at least one natural cyclodextrin selected from the group consisting of α-cyclodextrin, β-cyclodextrin and γ-cyclodextrin, the total concentration of the drug/cyclodextrin complex in the composition being above the aqueous solubility of the complex.

2. The method according to claim 1, wherein the drug is a corticosteroid, or wherein the drug is a carbonic anhydrase inhibitor, or wherein the drug is a GABA agonist, or wherein the drug is a growth factor inhibitor (anti-growth factor).

3. The method according to claim 1, wherein the drug is an antibiotic or wherein the drug is an antiviral agent.

4. The method according to claim 1, wherein the composition is in the form of eye drops, an eye mist or an eye gel.

5. The method according to claim 1, wherein the composition comprises from about 0.25% to about 40% of cyclodextrin, and further comprises up to about 5% (w/v) of water-soluble polymer, up to about 5% (w/v) of metal salts and up to about 5% (w/v) of organic salts, and optionally further comprises at least one buffer salt and/or at least one preservative.

6. The method according to claim 1, wherein the composition comprises from about 2% (w/v) to about 20% (w/v) of cyclodextrin, and further comprises from about 0.1% (w/v) to about 1% (w/v) of water-soluble polymer, up to about 2% (w/v) of metal salts and up to about 3% (w/v) of organic salts, and optionally further comprises at least one buffer salt and/or at least one preservative.

7. The method according to claim 5, wherein the metal salt has a divalent or trivalent cation and/or wherein the organic salt is a salt of or an ionized form of acetic acid, glutaric acid, a hydroxy acid or an amino acid.

8. The method according to claim 5, wherein the metal salt is a magnesium salt and/or wherein the organic salt is a salt of or the ionized form of citric acid, lactic acid, ascorbic acid, tartaric acid or lysine.

9. The method according to claim 7, wherein said magnesium salt is magnesium chloride.

10. The method according to claim 1, wherein the drug/cyclodextrin particles dissolve within from about 10 minutes to about 24 hours after administration to the eye surface.

11. The method according to claim 1, wherein the cyclodextrin further comprises at least one pharmaceutically acceptable cyclodextrin derivative selected from the group consisting of hydroxyalkyl-β-cyclodextrins, hydroxyalkyl-γ-cyclodextrins, randomly methylated-β-cyclodextrin, β-cyclodextrin sulfobutyl ether, γ-cyclodextrin sulfobutyl ether, branched β-cyclodextrin and branched γ-cyclodextrins.

12. The method according to claim 11, wherein the at least one pharmaceutically acceptable cyclodextrin derivative is hydroxypropyl-β-cyclodextrin, hydroxypropyl-γ cyclodextrin, randomly methylated β-cyclodextrin, β-cyclodextrin sulfobutyl ether, γ-cyclodextrin sulfobutyl ether or glucosyl-β-cyclodextrin.

13. The method according to claim 1, wherein the cyclodextrin comprises at least γ-cyclodextrin and/or wherein the cyclodextrin further comprises at least hydroxypropyl-γ-cyclodextrin.

14. The method according to claim 5, wherein said polymer is methylcellulose, hydroxyethyl cellulose, hydroxypropyl cellulose, hydroxypropyl methylcellulose, hydroxypropyl ethylcellulose, carboxymethylcellulose, polyvinyl alcohol, poly(methyl methacrylate), polycarbophil, gelatin, alginate, poly(acrylic acid), polyvinylpyrrolidone, polyethylene glycol, polyethylene oxide or chitosan.

15. The method according to claim 2, wherein said GABA agonist is a benzodiazepine.

16. The method according to claim 2, wherein said carbonic anhydrase inhibitor is dorzolamide, acetazolamide, methazolamide, ethoxyzolamide or brinzolamide; or wherein said corticosteroid is dexamethasone, hydrocortisone, triamcinolone, triamcinolone acetonide, prednisolone, fluorometholone, medrysone, rimexolone, loteprednol etabonate or etiprednol dicloacetate; or wherein said GABA agonist is baclofen, tiagabine, valproic acid, progabide, muscimol, etomidate, propofol, diazepam, alprazolam, brotizolam, chlordiazepoxide, clobazam, clonazepam, clorazepam, demoxazepam, flumazenil, flurazepam, halazepam, midazolam, nordazepam, mebazepam, nitrazepam, oxazepam, medazepam, lorazepam, prazepam, quazepam, triazolam, temezepam or lorazolam.

17. The method according to claim 1, wherein said cyclodextrin is a mixture of a natural α-, β- or γ-cyclodextrin and the corresponding water-soluble α-, β- or γ-cyclodextrin derivative selected from the group consisting of hydroxyalkyl-β-cyclodextrins, hydroxyalkyl-γ-cyclodextrins, randomly methylated β-cyclodextrin, the sulfobutyl ether of β-cyclodextrin, the sulfobutyl ether of γ-cyclodextrin, branched β-cyclodextrins and branched γ-cyclodextrins.

18. The method according to claim 17, wherein said water soluble derivative is selected from the group consisting of hydroxypropyl-β-cyclodextrin, hydroxypropyl-γ-cyclodextrin, randomly methylated β-cyclodextrin, the sulfobutyl ether of β-cyclodextrin, the sulfobutyl ether of γ-cyclodextrin, glucosyl β-cyclodextrin and glucosyl γ-cyclodextrin.

19. The method according to claim 17, wherein said cyclodextrin is a mixture of γ-cyclodextrin and 2-hydroxypropyl-γ-cyclodextrin, or a mixture of γ-cyclodextrin and the sulfobutyl ether of γ-cyclodextrin, or a mixture of β-cyclodextrin and 2-hydroxypropyl-β-cyclodextrin, or a mixture of β-cyclodextrin and the sulfobutyl ether of β-cyclodextrin, or a mixture of β-cyclodextrin and randomly methylated β-cyclodextrin.

20. The method according to claim 1, wherein the drug is triamcinolone acetonide or 2,5-dimethyl-2H-pyrazole-3-carboxylic acid {2-fluoro-5-[3-((E)-2-pyridin-2-ylvinyl)-1Hindazol-6-ylamino]phenyl}amide (AG013958), said composition being in the form of eye drops.

* * * * *